(12) United States Patent
Robinson et al.

(10) Patent No.: US 11,311,345 B2
(45) Date of Patent: Apr. 26, 2022

(54) CONTROL SYSTEM FOR CONTROLLING A SURGICAL ROBOT

(71) Applicant: CMR SURGICAL LIMITED, Cambridge (GB)

(72) Inventors: Duncan Robinson, Cambridge (GB); Edward James Wildin Tucker, Cambridge (GB); Gordon Thomas Deane, Cambridge (GB); Luke David Ronald Hares, Cambridge (GB); Rachel Marie Garsed, Cambridge (GB); Rebecca Anne Cuthbertson, Cambridge (GB); Ross Hamilton Henrywood, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 422 days.

(21) Appl. No.: 16/492,709

(22) PCT Filed: Mar. 9, 2018

(86) PCT No.: PCT/GB2018/050606
§ 371 (c)(1),
(2) Date: Sep. 10, 2019

(87) PCT Pub. No.: WO2018/162923
PCT Pub. Date: Sep. 13, 2018

(65) Prior Publication Data
US 2021/0145526 A1 May 20, 2021

(30) Foreign Application Priority Data

Mar. 10, 2017 (GB) ........................................ 1703878
Apr. 28, 2017 (GB) ...................................... 1706827

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/25* (2016.02); *A61B 34/74* (2016.02); *B25J 9/1689* (2013.01);
(Continued)

(58) Field of Classification Search
CPC combination set(s) only.
See application file for complete search history.

(56) References Cited

U.S. PATENT DOCUMENTS

| | | |
|---|---|---|
| 2007/0005045 A1 | 1/2007 | Mintz et al. |
| 2010/0228249 A1 | 9/2010 | Mohr et al. |
| (Continued) | | |

FOREIGN PATENT DOCUMENTS

JP    2008544814 A    12/2008

OTHER PUBLICATIONS

Notification of Transmittal of the International Search Report and the Written Opinion of the International Searching Authority from corresponding PCT/GB2018/050606 dated Jun. 8, 2018.
(Continued)

*Primary Examiner* — Scott Luan
(74) *Attorney, Agent, or Firm* — Lando & Anastasi, LLP

(57) ABSTRACT

A control system for controlling a surgical robot by a surgeon console remote from the surgical robot, the control system being configured to: receive one or more state signal associated with a plurality of instruments, each of the plurality of instruments being attachable to the surgical robot, the one or more state signal indicating a selectability of each of the plurality of instruments for control by the surgeon console, and a control mode of each of the plurality of instruments from a group of modes, the group of modes comprising a manipulation mode in which an instrument of the plurality of instruments is controllable by the surgeon console, and a selection mode in which an instrument of the plurality of instruments is selectable for control by the surgeon console; determine a graphical arrangement of icons for display in dependence on the received one or more state signal, where each icon represents a respective one of the plurality of instruments, and output a display signal to cause the graphical arrangement of icons to be displayed; receive a mode change signal indicating a change of mode to the selection mode; modify, in response to the received mode change signal, the graphical arrangement of icons to permit identification of selectable instruments of the plurality of instruments; receive a select signal from the surgeon console indicating a selection of one of the selectable instruments; modify, in response to the received select signal, the graphi- (Continued)

cal arrangement of icons to permit identification of the selected instrument; and enable control of the selected instrument by the surgeon console.

20 Claims, 11 Drawing Sheets

(51) Int. Cl.
      *B25J 9/16*     (2006.01)
      *G05B 19/042*     (2006.01)
      *A61B 17/00*     (2006.01)
      *B25J 13/04*     (2006.01)

(52) U.S. Cl.
    CPC .. *G05B 19/042* (2013.01); *A61B 2017/00199* (2013.01); *A61B 2034/742* (2016.02); *B25J 13/04* (2013.01); *G05B 2219/36076* (2013.01); *G05B 2219/45123* (2013.01)

(56) References Cited

U.S. PATENT DOCUMENTS

| | | |
|---|---|---|
| 2010/0228264 A1 | 9/2010 | Robinson et al. |
| 2014/0081455 A1 | 3/2014 | Goldberg et al. |
| 2015/0157411 A1 | 6/2015 | Choi |
| 2015/0351864 A1 | 12/2015 | Kamon et al. |

OTHER PUBLICATIONS

United Kingdom Search Report from corresponding United Kingdom Application No. GB1706827.1 dated Sep. 18, 2017.
English Translation of Japanese Notification of Reasons for Refusal from corresponding Japanese Application No. 2019-548926 dated Feb. 1, 2022.

CONTROL SYSTEM FOR CONTROLLING A SURGICAL ROBOT

CROSS-REFERENCE TO RELATED APPLICATIONS

This application is a U.S. National Phase Application under 35 U.S.C. § 371 of International Application No. PCT/GB2018/050606, filed Mar. 9, 2018, which claims priority to United Kingdom Application No. 1706827.1, filed Apr. 28, 2017 and United Kingdom Application No. 1703878.7, filed Mar. 10, 2017. Each application referenced above is hereby incorporated by reference in its entirety for all purposes.

BACKGROUND

This invention relates to control systems for controlling robots, such as surgical robots.

Robots are commonly used for a range of industrial tasks, and also for performing surgery. Robots can operate purely under programmatic control or they can be configured to respond to inputs in real time from a user interface. In the most complex and critical tasks, such as surgery, it is normal for a robot to operate under real-time command of an operator. To achieve this, the operator is presented with a suitable input device. This is typically a physical mechanism that can be moved by the operator in three dimensions. The control system of the robot senses the configuration of the input device. The control system is programmed to cause the robot arm/manipulator to move in response to the sensed configuration of the control mechanism. Additionally, it is normal for the robot to present to the user a visual indication of the state of the robot, to help the operator understand what inputs are required to achieve a certain task. The visual indication may be a video stream captured by a camera on or near the robot arm and presented to the operator on a display screen.

The robot can include a plurality of arms. Each arm can have an instrument at its distal end which can be operated by the operator to carry out desired tasks.

Where more than one arm is present, the robot can indicate to the operator which arm is being controlled. For instance, for two arms, the robot can indicate to the operator which arm is being controlled by the operator's left hand (i.e. by a left-hand controller) and which arm is being controlled by the operator's right hand (i.e. by a right-hand controller). One way of doing this is to cause the robot to show an image of the instrument being operated by the operator on the display. The image can be shown on the left or right of the display to indicate whether it is being controlled by the left or right hand (or left or right input device).

In some situations the operator will need to shift their attention away from the video stream to check the status of the arm or instrument, and when trying to change which instrument they are controlling. This can mean that the operator is not, at that time, paying sufficient attention to the video stream. This risks operator error when controlling the robot.

There is a need for an improved control system.

SUMMARY

According to an aspect of the present invention there is provided a control system for controlling a surgical robot by a surgeon console remote from the surgical robot, the control system being configured to: receive one or more state signal associated with a plurality of instruments, each of the plurality of instruments being attachable to the surgical robot, the one or more state signal indicating a selectability of each of the plurality of instruments for control by the surgeon console, and a control mode of each of the plurality of instruments from a group of modes, the group of modes comprising a manipulation mode in which an instrument of the plurality of instruments is controllable by the surgeon console, and a selection mode in which an instrument of the plurality of instruments is selectable for control by the surgeon console; determine a graphical arrangement of icons for display in dependence on the received one or more state signal, where each icon represents a respective one of the plurality of instruments, and output a display signal to cause the graphical arrangement of icons to be displayed; receive a mode change signal indicating a change of mode to the selection mode; modify, in response to the received mode change signal, the graphical arrangement of icons to permit identification of selectable instruments of the plurality of instruments; receive a select signal from the surgeon console indicating a selection of one of the selectable instruments; modify, in response to the received select signal, the graphical arrangement of icons to permit identification of the selected instrument; and enable control of the selected instrument by the surgeon console.

Suitably the graphical arrangement of icons comprises: a list region in which an icon representing one of the plurality of instruments is caused to be displayed prior to the change of mode to the selection mode, and a selection region in which an icon representing a selectable instrument of the plurality of instruments is caused to be displayed in the selection mode; the list region and the selection region being at least partially non-overlapping.

The graphical arrangement of icons may comprise an image region for displaying an image of a surgical site, the image region being provided towards a centre of the graphical arrangement of icons, and in which the selection region is provided so as to at least partially overlap the image region. Suitably the list region is provided one of at and towards a periphery of the graphical arrangement of icons. Suitably the list region is at least partially non-overlapping with the image region.

Suitably the list region comprises a new instrument region in which an icon representing a newly-added instrument is caused to be displayed, the new instrument region being provided so as to at least partially overlap the image region.

Suitably the control system is configured, in response to receiving the mode change signal, to cause a transition of the icon representing the selectable instrument to the selection region to indicate that the respective instrument is selectable. Suitably the control system is configured to cause the transition to be a continuous transition.

Suitably the control system is configured to receive the mode change signal from at least one of the surgeon console and the surgical robot. Suitably the control system is configured, in response to receiving the mode change signal, to change to the selection mode from one of the manipulation mode and a setup mode in which an instrument of the plurality of instruments is set up for operative coupling to the surgeon console.

Suitably the control system is configured to receive an input signal from each of a plurality of input devices of the surgeon console, the graphical arrangement of icons comprising a plurality of selection regions with each input device being associated with a respective one of the plurality of selection regions, the control system being configured, in response to receiving the mode change signal, to cause icons representing instruments selectable by each input device to be displayed in the respective selection region for that input device.

Suitably the modification to the graphical arrangement of icons permitting identification of the selectable instruments comprises one or more of: changing the colour of an icon, changing the size of the icon, changing the background of the icon, changing the icon from a two-dimensional icon to a three-dimensional icon, changing the icon from a three-dimensional icon to a two-dimensional icon, causing the icon to flash, and causing the icon to flash with a modified frequency.

Suitably the control system is configured to receive an image signal representative of an image from a surgical site, and to cause the display of the image in the image region, the displayed image comprising an instrument image of an instrument at the surgical site, and the control system being configured to modify the instrument image in response to receiving the mode change signal.

Suitably the control system is configured to modify the instrument image by at least one of overlaying graphics on the image region, modifying graphics overlaid on the image region, and removing graphics overlaid on the image region. Suitably the control system is configured to modify the instrument image to correspond to the modification to the graphical arrangement of icons permitting identification of the selectable instruments.

Suitably at least one of the list region, the selection region and the new instrument region comprises a border around at least a portion of its periphery, and the control system is configured to modify the border in response to receiving the mode change signal to permit identification of the change of mode.

Suitably the control system comprises a kinematics controller configured to determine an interface state in dependence on the one or more state signal associated with the plurality of instruments, the interface state comprising data associated with the graphical arrangement of icons for display.

Suitably the control system comprises a visual processor configured to receive the interface state from the kinematics controller and to render the graphical arrangement of icons for display, the kinematics controller being operable at a higher frequency than the visual processor.

Suitably icon of the graphical arrangement of icons comprises a cluster of icons.

According to another aspect of the present invention there is provided a method for controlling a surgical robot by a surgeon console remote from the surgical robot, the method comprising: receiving one or more state signal associated with a plurality of instruments, each of the plurality of instruments being attachable to the surgical robot, the one or more state signal indicating the selectability of each of the plurality of instruments for control by the surgeon console, and a control mode of each of the plurality of instruments from a group of modes, the group of modes comprising a manipulation mode in which an instrument of the plurality of instruments is controllable by the surgeon console, and a selection mode in which an instrument of the plurality of instruments is selectable for control by the surgeon console; determining a graphical arrangement of icons for display in dependence on the received one or more state signal, where each icon represents a respective one of the plurality of instruments, and outputting a display signal to cause the graphical arrangement of icons to be displayed; receiving a mode change signal indicating a change of mode to the selection mode; modifying, in response to the received mode change signal, the graphical arrangement of icons to permit identification of selectable instruments of the plurality of instruments; receiving a select signal from the surgeon console indicating a selection of one of the selectable instruments; modifying, in response to the received select signal, the graphical arrangement of icons to permit identification of the selected instrument; and enabling control of the selected instrument by the surgeon console.

According to another aspect of the present invention there is provided machine readable code for implementing a method as defined herein.

Any one or more feature of any aspect above may be combined with any one or more feature of any other aspect above. Any apparatus feature may be written as a method feature where possible, and vice versa. These have not been written out in full here merely for the sake of brevity.

This Summary is provided to introduce a selection of concepts in a simplified form that are further described below in the Detailed Description. The mention of features in this Summary does not indicate that they are key features or essential features of the invention or of the claimed subject matter, nor is it to be taken as limiting the scope of the claimed subject matter.

BRIEF DESCRIPTION OF DRAWINGS

The present invention will now be described by way of example only with reference to the accompanying drawings. In the drawings.

DETAILED DESCRIPTION

The following description describes the present techniques in the context of surgical robotic systems, though the features described below are not limited to such systems, but are applicable to robotic systems more generally.

Robotic systems can include manufacturing systems, such as vehicle manufacturing systems, parts handling systems, laboratory systems, and manipulators such as for hazardous materials or surgical manipulators.

Figure 1:
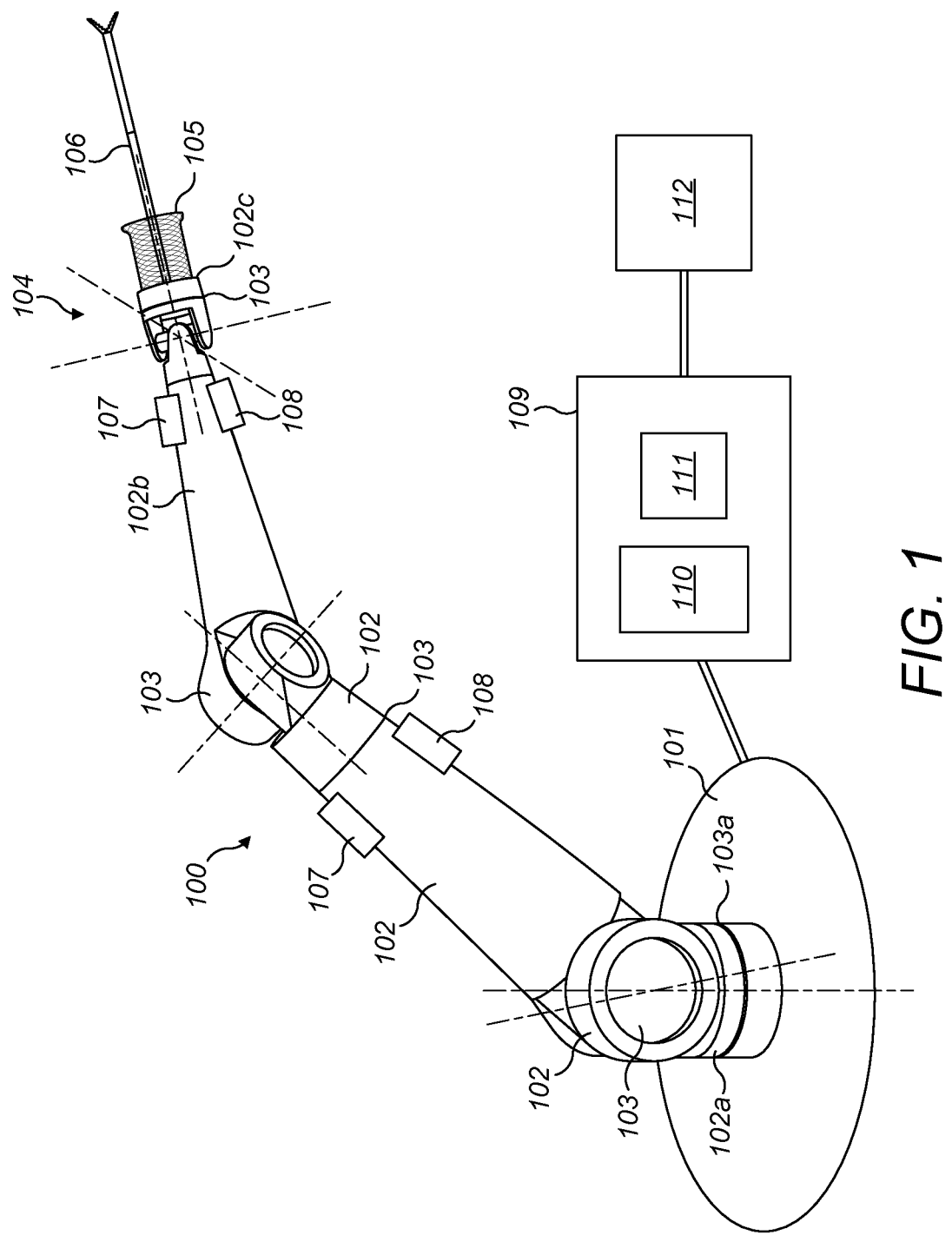
FIG. 1 illustrates a surgical robot arm.

FIG. 1 illustrates a surgical robot having an arm 100 which extends from a base 101. The arm comprises a number of rigid limbs 102. The limbs are coupled by revolute joints 103. The most proximal limb 102a is coupled to the base by a proximal joint 103a. It and the other limbs are coupled in series by further ones of the joints 103. Suitably, a wrist 104 is made up of four individual revolute joints. The wrist 104 couples one limb (102b) to the most distal limb (102c) of the arm. The most distal limb 102c carries an attachment 105 for a surgical instrument 106. Each joint 103 of the arm has one or more motors 107 which can be operated to cause rotational motion at the respective joint, and one or more position and/or torque sensors 108 which provide information regarding the current configuration and/or load at that joint. Suitably, the motors are arranged proximally of the joints whose motion they drive, so as to improve weight distribution. For clarity, only some of the motors and sensors are shown in FIG. 1. The arm may be generally as described in our co-pending patent application PCT/GB2014/053523 (published as WO/2015/132549).

Figure 2:
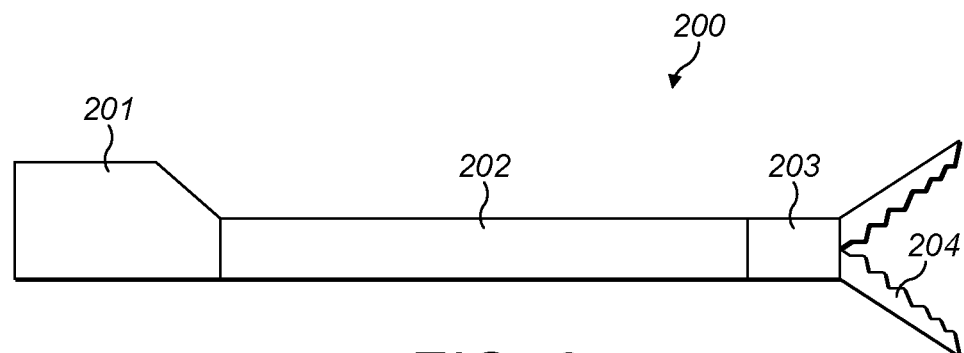
FIG. 2 illustrates an instrument for use with the arm of FIG. 1.

The arm terminates in the attachment 105 for interfacing with the instrument 106. Suitably, the instrument 106 takes the form described with respect to FIG. 2. FIG. 2 illustrates a typical surgical instrument 200 for performing robotic laparoscopic surgery. The surgical instrument comprises a base 201 by means of which the surgical instrument connects to the robot arm. A shaft 202 extends between the base 201 and an articulation 203. The articulation 203 terminates in an end effector 204. In FIG. 2, a pair of serrated jaws are illustrated as the end effector 204. The articulation 203 permits the end effector 204 to move relative to the shaft 202. It is desirable for at least two degrees of freedom to be provided to the motion of the end effector 204 by means of the articulation.

The instrument has a diameter less than 8 mm. Suitably, the instrument has a 5 mm diameter. The instrument may have a diameter which is less than 5 mm. The instrument diameter may be the diameter of the shaft. The instrument diameter may be the diameter of the profile of the articulation. Suitably, the diameter of the profile of the articulation matches or is narrower than the diameter of the shaft. The attachment 105 comprises a drive assembly for driving articulation of the instrument.

The instrument 106 comprises an end effector for performing an operation. The end effector may take any suitable form. For example, the end effector may be smooth jaws, serrated jaws, a gripper, a pair of shears, a needle for suturing, a camera, a laser, a knife, a stapler, a cauteriser, a suctioner. As described with respect to FIG. 2, the instrument comprises an articulation between the instrument shaft and the end effector. The articulation comprises several joints which permit the end effector to move relative to the shaft of the instrument.

Controllers for the motors, torque sensors and encoders are distributed within the robot arm. The controllers are connected via a communication bus to a control unit 109. The control unit 109 comprises a processor 110 and a memory 111. The memory 111 stores in a non-transient way software that is executable by the processor to control the operation of the motors 107 to cause the arm 100 to operate. In particular, the software can control the processor 110 to cause the motors (for example via distributed controllers) to drive in dependence on inputs from the sensors 108 and from a surgeon command interface 112. The control unit 109 is coupled to the motors 107 for driving them in accordance with outputs generated by execution of the software. The control unit 109 is coupled to the sensors 108 for receiving sensed input from the sensors, and to the command interface 112 for receiving input from it. The respective couplings may, for example, each be electrical or optical cables, or may be provided by a wireless connection. The command interface 112 comprises one or more input devices whereby a user can request motion of the end effector in a desired way. The input devices, or input controllers, could, for example, be manually operable mechanical input devices such as control handles or joysticks, touch-operable inputs such as touchscreens, or contactless input devices such as optical gesture sensors or voice sensors. The input devices might monitor eye movement to receive an input. The input devices could, for example, be some combination of these types of input devices. Commands input by the input devices can include movement commands, for example to move the instrument in a particular way, such as a lateral movement and/or a rotation. Such commands can include end effector commands, for example to control an end effector coupled to a distal end of the instrument to operate the end effector, such as to open/close gripper jaws or to operate (turn on or off) an electrosurgical end effector.

Suitably a user console, such as a surgeon console, comprises the command interface 112. Suitably, the user console comprises two input devices.

The input device may be associated with one of a left-hand control and a right-hand control. Suitably, where there are a plurality of input devices, one of the input devices is associated with a left-hand control and another of the input devices is associated with a right-hand control. In other words, one of the input devices may be configured to be operated by a user's right hand (a right-hand control, which is suitably provided towards the right-hand side of the user console) and another of the input devices may be configured to be operated by a user's left hand (a left-hand control, which is suitably provided towards the left-hand side of the user console).

The software stored in the memory 111 is configured to respond to those inputs and cause the joints of the arm and instrument to move accordingly, in compliance with a predetermined control strategy. The control strategy may include safety features which moderate the motion of the arm and instrument in response to command inputs. Thus, in summary, a surgeon at the surgeon console which suitably comprises the command interface 112 can control the instrument 106 to move in such a way as to perform a desired surgical procedure. The control unit 109 and/or the command interface 112 may be remote from the arm 100.

Figure 3A:
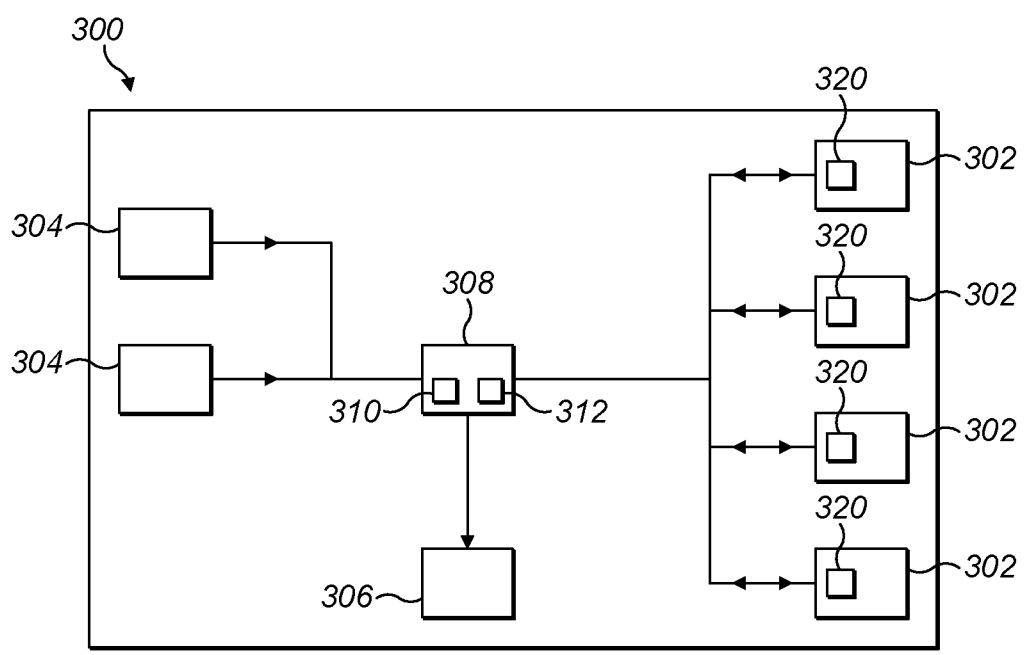
FIG. 3A illustrates a schematic of a robotic surgical system.

A schematic of a robotic surgical system will now be described with reference to FIG. 3A. A robotic surgical system 300 comprises a surgical robot which comprises a plurality of robot arms 302, a plurality of (usually two) input devices 304, a display device 306 such as a screen and a control system 308. The control system 308 suitably comprises the control unit 109. The control system 308 may comprise a plurality of processors. The control system suitably comprises a kinematics controller 310 and a visual processor 312. The robot arms 302 are provided with surgical instruments, and/or other implements, 320 such as grippers, cutters, cauterizers, needles, imaging devices (for example a camera such as an endoscope), or the like, at their distal ends. The robot arms 302, input devices 304 and the screen 306 are operatively connected to the control system 308. The control system 308 is responsive to signals received from the surgeon console (such as from the input devices 304), the robot arms 302 and the instruments 320, and can provide signals to the robot arms 302, the instruments 320 and the screen 306. The control system 308 receives the signals from the surgeon console and processes the signals so as to output drive signals for driving one or more of the robot arms 302 and/or one or more of the instruments 320. The drive signals are sent by the control system to the respective robot arms 302 and instruments 320.

Suitably the imaging device is configured to output an image signal. Suitably the image signal comprises an image. The image signal suitably comprises a video signal.

Whilst the above description refers to a single screen as a display device, in some examples the robotic surgical system comprises a plurality of display devices, or screens. The screens are suitably configured to display the image as a two-dimensional image and/or as a three-dimensional image. The screens can be provided on a single user console, or two or more consoles can comprise at least one screen each. This permits additional viewing screens which can be useful for allowing people other than the console user to view the surgical site, for example for training, and/or for viewing by other people in the operating room.

Figure 4:
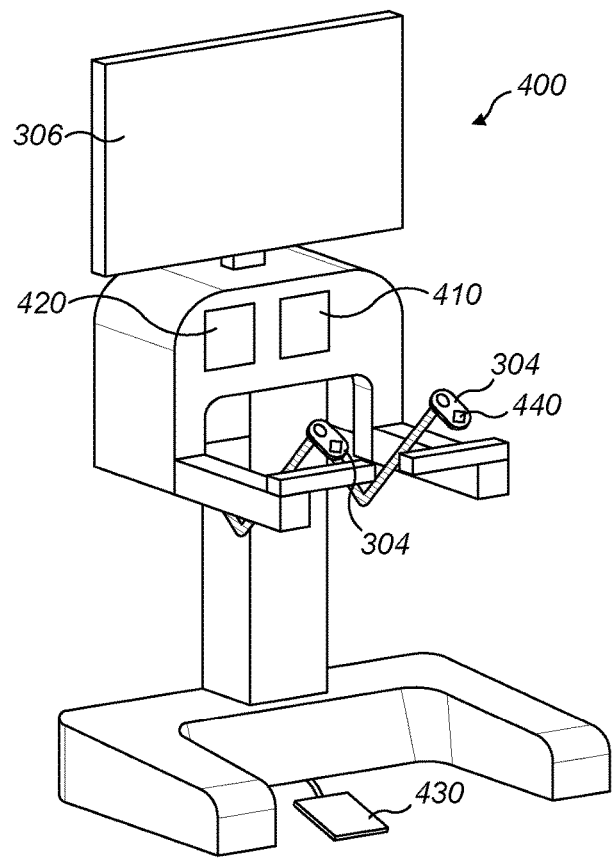
FIG. 4 illustrates a surgeon console.

An example illustration of a user console such as a surgeon console 400 is shown in FIG. 4. A user such as a surgeon can control the robot arms 302 and the instruments 320 coupled to the robot arms 302 via the input devices 304 at the surgeon console 400 and can manipulate the robot arms and/or the instruments as desired. As illustrated in FIG. 4, the surgeon console 400 comprises a contactless input device 410 which comprises at least one of a gesture sensor such as an optical gesture sensor and a voice sensor. The surgeon console 400 comprises a touchscreen input device 420. Additionally or alternatively, the display 306 may comprise a touchscreen input. The surgeon console 400 comprises a foot-operable input device 430 such as a foot pedal. One of each of devices 410, 420, 430 are shown in FIG. 4, but it will be appreciated that any numbers of any combination of these devices may be provided in other examples. Not all input devices, or all types of input devices, need be provided in all examples.

Manipulation of the instruments 320 includes manipulation or operation of the end effector of the instrument. In other words, opening or closing jaws of an end effector, or activating or deactivating an electrosurgical tool such as a cauteriser.

Suitably the robot arms 302 and/or instruments 320 are configured to send a signal to the control system 308. In some examples, this signal comprises one or more state signal. In some examples, this signal comprises position and/or orientation signals indicative of the respective robot arm 302 or instrument 320 position and/or orientation. The signal may comprise one or more force signal indicative of a force on one or both of the respective robot arm 302 and instrument 320.

In the foregoing, the robotic system may be configured to send and receive signals by wired connections. Suitably the robotic system comprises one or more wireless transceivers to wirelessly transmit and/or receive signals. This permits a reduction in the need for wired connections through the robotic system. Suitably the robotic system is configured to send and/or receive signals by wireless and/or wired signals.

Suitably at least one of the input devices 304 and the robot arms 302 comprise a first wireless transmitter, a first wireless receiver and/or a first wireless transceiver. Suitably the control system comprises a second wireless transmitter, a second wireless receiver and/or a second wireless transceiver for communicating with the respective one of the first wireless receiver, first wireless transmitter and/or first wireless transceiver. Suitably the instrument 320 comprises the respective one of the first wireless transmitter, first wireless receiver and/or first wireless transceiver.

Figure 5:
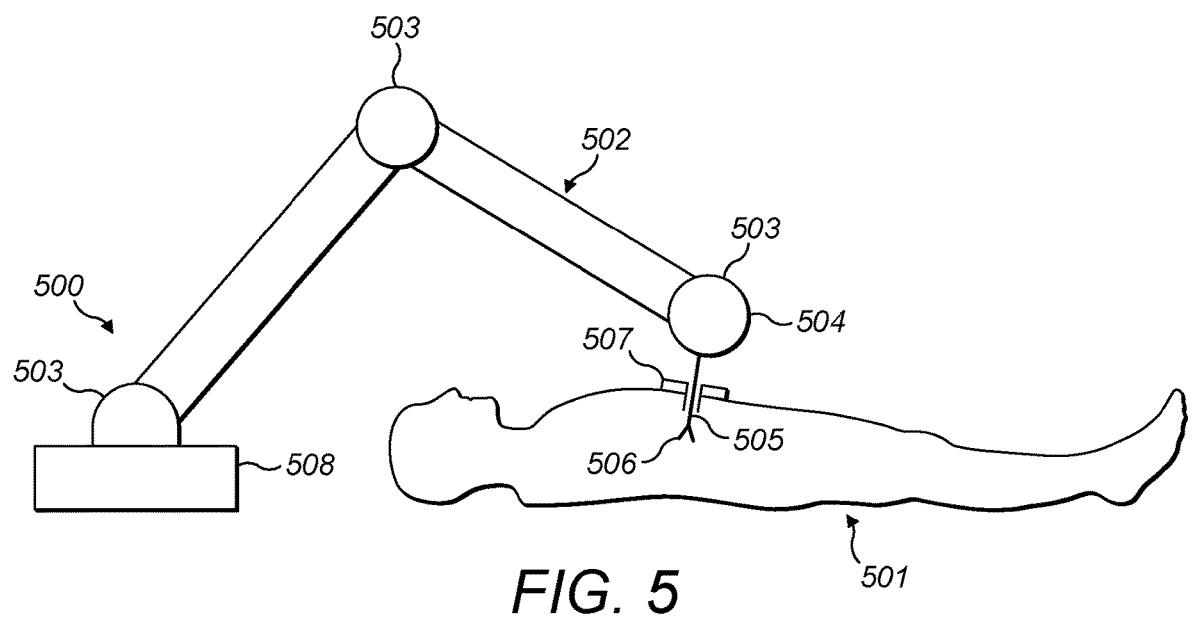
FIG. 5 illustrates a surgical robot.

The user may be remote from the arms 302 and the instruments 320, and so may not be able to see them directly. The instruments 320 may be embedded within a surgical site, preventing direct observation. An example of such a set-up is illustrated in FIG. 5. FIG. 5 illustrates a typical surgical robot 500 which consists of a base 508, an arm 502, and an instrument 505. The base supports the robot, and is itself attached rigidly to, for example, the operating theatre floor, the operating theatre ceiling or a trolley. The arm extends between the base and the instrument. The arm is articulated by means of multiple flexible joints 503 along its length, which are used to locate the surgical instrument in a desired location relative to the patient. The surgical instrument is attached to the distal end 504 of the robot arm. The surgical instrument penetrates the body of the patient 501 at a port 507 so as to access the surgical site. At its distal end, the instrument comprises an end effector 506 for engaging in a medical procedure.

Whilst FIG. 5 illustrates a single arm with a single instrument, in practice multiple arms and instruments will be used. One arm is coupled to an imaging device which provides image signals representative of the surgical site. For example, the imaging device can be an endoscope. The endoscope can provide an image feed, such as a video stream, from the surgical site. The image provided by the imaging device enables the user to see the end effectors at the surgical site, for example via the display device 306. This enables the user or operator of the robotic surgical system 300, such as a surgeon, to effect control over the instruments to effect surgery.

In many surgical procedures it is desirable for the user to be able to select from among two or more instruments 320. For example, an input device 304 is usable to control a plurality of instruments 320. The input device 304 is usable to control one instrument when coupled to the one instrument, and is usable to control another instrument when coupled to that other instrument. In other words, an input device 304 is usable to control the instrument 320 to which it is operatively coupled. The coupling between input device and instrument is changeable. One instrument can be controlled by a plurality of input devices. The instrument is couplable to one input device to permit control of the instrument by the one input device. Once decoupled from the one input device, the instrument is couplable to another input device to permit control of the instrument by that other input device. More than one instrument 320 can be operatively associated with a single input device 304.

Generally, the surgeon console is operatively couplable to one or more instrument, to permit or enable control of the instrument by the surgeon console. Suitably the surgeon console is operatively couplable to a plurality of instruments so as to enable control of more than one instrument at a time. For example, the surgeon console can be operatively couplable to three or more instruments, and can enable two of those instruments to be controlled at once. In other examples, more instruments can be controlled at once. The surgeon console can, for example, enable control of two surgical tools and an endoscope at once.

Figure 3B:
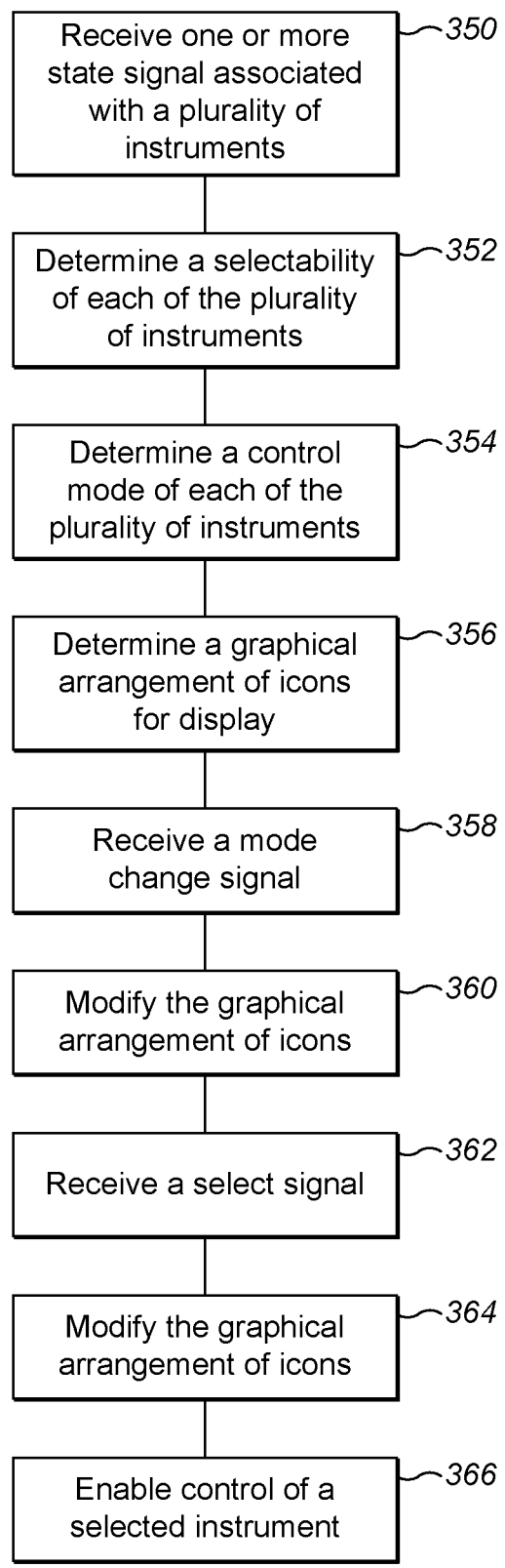
FIG. 3B illustrates an example method using the robotic surgical system.

The instrument or plurality of instruments has associated therewith one or more state signal. In one example, each instrument is configured to output a respective state signal. The one or more state signal may comprise a signal indicating the state of a plurality of instruments. The one or more state signal may comprise a signal indicating the state of a single instrument. The control system 308 is configured to receive the one or more state signal (reference is made to FIG. 3B, showing method steps, at 350).

The one or more state signal indicates a selectability of an instrument or of each of the plurality of instruments for control by the surgeon console. This means that the control system is able to determine the selectability of the instrument or of each instrument (step 352). In one example the one or more state signal can indicate that an instrument is coupled to the surgical robot, and is able to receive commands from the control system, such as commands from the surgeon console via the control system, and that the instrument is able to respond to those commands accordingly.

In some examples, the state of the instrument comprises at least one of an instrument identification, a power state of the instrument, such as an internal power state of a battery and/or another component, or a power state of a powered tool such as a cauteriser. Suitably, where the state of the instrument indicates that power is unavailable to a powered tool, that instrument is not selectable by the control system.

The state of the instrument may comprise a temperature of the instrument or the temperature of a portion of the instrument. Suitably, where the state of the instrument indicates that the temperature is outside an operating range (for example the instrument may have overheated), that instrument is not selectable by the control system. The operating range for the temperature is suitably predetermined and/or user-selectable.

The state of the instrument suitably comprises the number of times that that instrument has been used before or a time (such as a cumulative time) of use of the instrument, the number of uses remaining for that instrument and/or a lifetime remaining for that instrument. Suitably, where the state of the instrument indicates that the instrument should no longer be used (for example because it has exceeded a predetermined number of times of use, or a predetermined time (such as a cumulative time) of use), that instrument is not selectable by the control system.

The state of the instrument suitably comprises a fault condition. The fault condition suitably indicates the occurrence of a fault in the operation of the arm and/or of the instrument. The fault can be in the present or the past. That is, the situation causing the fault may be ongoing, or it may have stopped. For example, the arm and/or instrument may experience a force above a threshold force. Forces above the threshold force may indicate that cable stretch has occurred, or is likely to have occurred. The fault condition can indicate that the arm and/or instrument is experiencing a force above the threshold force. The fault condition can indicate that the arm and/or instrument has experienced a force above the threshold force in its history, i.e. at some point in the past, for example since being coupled to the system.

Suitably, the control system is configured to determine, in dependence on the one or more state signal, whether the instrument is selectable.

The state of the instrument may comprise a configuration of the instrument, including one or more of a joint state signal and an end effector signal. The joint state signal suitably indicates an orientation and/or torque of a joint, and/or a force on the joint. The end effector signal suitably indicates an orientation and/or a configuration of an end effector of the instrument, such as whether jaws of a gripper are open or closed, and/or a force on the end effector.

In some examples, at least one instrument of the plurality of instruments is configured to output the one or more state signal. Suitably, the at least one instrument is configured to output the one or more state signal in dependence on the state of the instrument or of a plurality of instruments. The state of the instrument may comprise the arrangement of the end effector (where the end effector is movable). In other words, where the end effector is a gripper, the state of the instrument may comprise the state of the gripper: whether it is open, closed, or in some intermediate configuration. For example, the state of the instrument comprises the angle of separation of the jaws of the gripper. Suitably where the end effector comprises separate elements, such as jaws, the separate elements are separately controllable. For example each of a pair of jaws are independently controllable. Suitably the state of the instrument comprises a state of each of the separate elements, such as the jaws. Where the end effector comprises an electrosurgical tool, the state of the instrument suitably comprises the activation state of the electrosurgical tool, for example whether the tool is electrically activated, not electrically activated, and/or other related information such as the temperature of the tool (noting that after electrical activation, the temperature of the tool will remain elevated for a given period of time). Suitably, the state of the instrument comprises an indication of whether the electrosurgical tool is in a 'cut' mode or a 'coagulation' mode.

Suitably the or each instrument comprises one or more sensor to determine at least a portion of the state of the instrument. The at least one instrument is suitably configured to transmit the one or more state signal to the control system.

The one or more state signal, in some examples, comprises a compatibility signal, indicating the compatibility of the instrument with the surgeon console and/or the surgical robot. The compatibility signal may be used to verify that the instrument is compatible with the surgeon console and/or with the surgical robot, and in dependence on determining that the instrument is compatible, to permit the instrument to be selectable by the control system.

An instrument may be selectable for control by the surgeon console where it is coupled or mounted to the surgical robot. The instrument may be selectable by the surgeon console when it has undergone any one or more of necessary post-coupling checks, such as software initialisation routines, setup checks, configuration checks and so on, re-inserted into a port, and advanced towards a surgical site. An instrument may not be selectable immediately on coupling to the surgical robot. In preferred examples, post-coupling checks suitably take less than 30 seconds to complete, and preferably take less than 20 seconds to complete, for example they may take less than 10 seconds to complete.

An instrument is associated with a control mode. The control mode indicates a mode of control or operation of the instrument. Suitably there is a group of modes comprising a plurality of control modes.

The group of modes comprises a manipulation mode, in which an instrument is controllable by the surgeon console. The instrument may be controllable by the surgeon console when it is operatively coupled to the surgeon console. Suitably, in the manipulation mode, input commands input at the surgeon console, such as signals from an input device, cause control of the instrument to be effected. For example, an input signal at an input device to move an instrument laterally can cause the control system to output a control signal to the surgical robot to cause the respective instrument to undergo a corresponding lateral move. In the manipulation mode, the control system operatively couples the surgeon console to an instrument.

The group of modes comprises a selection mode, in which an instrument is selectable for control by the surgeon console. Suitably, in the selection mode, a plurality of instruments are selectable for control by the surgeon console.

The one or more state signal indicates a control mode of an instrument or of each of the plurality of instruments from the group of modes, the group of modes comprising the manipulation mode and the selection mode. This means that the control system is able to determine which control mode an instrument is in. Suitably the control system is configured to determine a control mode of each of the plurality of instruments (step 354).

The association or coupling is suitably indicated to the user at the surgeon console. This can be via the display device 306. Suitably the control system 308 is configured to cause the display device to display a graphical representation of the instruments so as to permit the user to identify, inter alia, which instruments are connected to the system, which of those instruments is/are available for control by the surgeon console 400, which instrument is currently selected by the surgeon console (or which instruments are currently selected by the surgeon console where two or more input devices are provided), and whether an instrument is in a manipulation mode in which it is able to be manipulated or controlled by the surgeon console or whether the instrument is in a selection mode in which it is able to be selected for control by the surgeon console. Suitably the control system 308 is configured to cause the display device to display a graphical representation of the instruments so as to permit the user to identify, in the manipulation mode, which instrument or instruments are controllable by the surgeon console. Suitably the control system 308 is configured to cause the display device to display a graphical representation of the instruments so as to permit the user to identify, in the selection mode, which instrument or instruments are selectable by the surgeon console.

The control system 308 is configured to determine a graphical arrangement of icons for display (step 356) in dependence on the received one or more state signal. Each icon represents a respective one of the plurality of instruments. For example, a first icon represents a first instrument and a second icon represents a second instrument. Similarly, one or more further icon represents a respective one or more further instrument. The control system 308 is configured to output a display signal to cause the graphical arrangement of icons to be displayed.

Where the surgeon console 400 comprises more than one input device, the control system 308 is suitably configured to cause the display device 306 to display the graphical arrangement of icons so as to permit the user to identify which instrument or instruments is controllable by one of the input devices. For example, where left-hand and right-hand input devices are provided, the control system may indicate which of the instruments is selectable by the left-hand input device and which of the instruments is selectable by the right-hand input device.

Suitably the icon, or each icon, comprises at least one of an image, a pictogram and an ideogram. Suitably the control system is configured to cause the icon to comprise at least one of an image, a pictogram and an ideogram. The icon can be two-dimensional or three-dimensional. The icon suitably comprises a representation of the end effector of the instrument. The icon may comprise a static representation of the instrument and/or end effector. The icon may comprise a dynamic representation of the instrument and/or end effector. An example of a dynamic representation is one that is shown in the same orientation as the instrument and/or end effector itself is shown in the image feed. This is a dynamic representation as it is able to change with time.

Suitably, the icon is coloured to match a colour of at least one of the end effector, the instrument, and the robot arm to which that instrument is mounted. The instrument suitably comprises a shaft extending from the end effector (or from an articulation to which the end effector is coupled) to a base of the instrument. The end effector is insertable into a surgical site. The base of the instrument couples to a robot arm. The base is thus not at the surgical site. The shaft of the instrument extends from an exterior to the surgical site, into the patient and towards the surgical site. Thus, different parts of the instrument may be visible in different ways. For example, the base of the instrument will be visible to operating room (OR) staff directly. A portion of the instrument shaft exterior to the patient will also be visible to OR staff directly. The end effector (when at a surgical site inside a patient) will not be directly visible, but may be viewed via the image displayed on the display, as captured by the imaging device. A portion of the instrument shaft interior to the patient will not be directly visible but may be viewed via the image displayed on the display. Suitably the icon is coloured to match one or more portion of the instrument (i.e. the base, portions of the shaft, the articulation and the end effector). This is described in more detail below. Thus the icon displayed in the graphical arrangement of icons permits identification of the instrument which that icon represents.

As discussed above, the group of modes comprises a manipulation mode and a selection mode. The control system 308 is suitably configured to control a change of mode to the selection mode in response to receiving a mode change signal. The control system 308 is configured to receive the mode change signal from one or both of the surgeon console and the robot arm (step 358). The robot arm is suitably configured to output the mode change signal, for example in response to the operation of a control or input device at the robot arm such as a button or switch). In this way, a member of OR staff can operate the control to cause the robot arm to output the mode change signal. Suitably the surgeon console 400 is configured to output the mode change signal. For example, the surgeon console is configured to output the mode change signal on operation, such as by a user, of a control of the surgeon console. Suitably, an input device 304 is configured to output the mode change signal. For example, a button or other control of the input device 304 is configured to cause the surgeon console to output the mode change signal. In this way, a surgeon at the surgeon console can choose to enter the selection mode by pressing the button or operating the other control. The surgeon at the surgeon console is able to enter a command at the surgeon console to cause the output by the surgeon console of the mode change signal.

An instrument may enter the selection mode in response to the mode change signal received at the control system 308. The instrument may enter the selection mode from the manipulation mode, or from another mode of the group of modes. The instrument may enter the selection mode from a setup or startup mode. Suitably the setup or startup mode is a mode in which the surgical robot, the surgeon console, the control system, and/or an instrument undergoes a startup routine in preparation for operation or operative coupling to at least one other portion of the system. Suitably, the setup mode is a mode in which an instrument of the plurality of instruments is set up for operative coupling to the surgeon console. Suitably the group of modes comprises the setup mode. The instrument may enter the selection mode from a new instrument mode in which an instrument is newly-added to the system. This will be described in more detail below. Suitably the group of modes comprises the new instrument mode.

The control system 308 is configured, in response to the received mode change signal, to modify the graphical arrangement of icons (step 360). The modification is such as to permit identification of a selectable instrument or of selectable instruments. Modifying the graphical arrangement of icons is not limited to modifying the layout only of the icons, but includes modifying the icons themselves, and/or modifying other aspects of the displayed image, such as how the icons appear, the orientation of the icons, and so on. This is discussed in more detail below in the context of examples of such modifications.

Suitably, the control system 308 is configured to determine, in dependence on the received mode change signal, which instrument or instruments are selectable for control by the surgeon console 400.

The surgeon console is suitably configured to select the selectable instrument, or select between the selectable instruments, by providing a select signal to the control system. The select signal indicates which of the selectable instruments is to be selected for operative control by the surgeon console. The select signal is suitably provided from an input device at the surgeon console, for example a manually operated input device 304. A user may suitably operate a control on the input device 304, for example a joystick control, a button control, a touch control and/or a trigger control, so as to cause the surgeon console to output the select signal. The surgeon console is suitably configured to output the select signal to the control system. The control system is suitably configured to receive the select signal (step 362).

The selection can be made at the surgeon console 400 to select the associated icon for the desired instrument from the selection region. The input device 304 itself need not be used to make this selection. Another button or control, such as a foot pedal 430 or switch at the surgeon console 400, can be used instead of or as well as the input device 304. This provides flexibility in the selection of the instrument. In a typical system, there are permitted to be as many active instruments at one time as there are input devices 304. For example, where two input devices 304 are provided, there can be up to two active instruments 320 at a time.

The control system 308 may be configured to permit each input device 304 to select the instrument 320 which is to be operatively coupled to that input device 304. The control system 308 may be configured to permit an input device 304 to select an instrument 320 which is to be operatively coupled to another input device 304.

The selection of the selectable instrument can be done in any convenient way. For example, the instrument to be selected can be indicated by a highlight of the icon representing that instrument. The icon can, for example, be highlighted by changing an aspect of the icon such as its colour, size and/or background. For example, the icon can be caused to flash. The icon can, for example, be highlighted by modifying its position within the display, for example by moving to the top (or other predefined position) of a list of icons. In one example, a highlighted icon can be positioned within a 'selection box' which might remain in one location in the displayed graphical arrangement of icons to indicate that the instrument represented by that icon is to be selected. Suitably the surgeon console can cause the icon highlight to cycle through the icons representing the selectable instruments. This permits the desired instrument to be selected. Suitably an icon can be highlighted by causing the display of an indicator, such as an arrow or similar, adjacent the icon. The indicator can be moved in response to user input to change which icon is highlighted. The indicator suitably indicates whether the highlighted icon is highlighted with respect to the right-hand input device or the left-hand input device. Suitably, the indicator is provided to the left of the icon to indicate that that icon is highlighted with respect to the left-hand input device. Suitably, the indicator is provided to the right of the icon to indicate that that icon is highlighted with respect to the right-hand input device.

Once the desired instrument is highlighted or otherwise indicated, the selection of that instrument can be confirmed. Suitably the select signal comprises a first select signal to indicate the instrument to be selected and a second select signal to confirm the selection. This permits a user such as a surgeon at the surgeon console to move between the selectable instruments and then to select the desired instrument. The control system 308 is configured, in response to the received select signal, to modify the graphical arrangement of icons (step 364). The modification is such as to permit identification of the selected instrument. Examples of such modifications are discussed below.

The control system 308 is configured, in response to receiving the select signal, to enable control of the selected instrument by the surgeon console 400 (step 366). This can be effected by enabling an operative coupling between the selected instrument and the surgeon console. The operative coupling between the selected instrument and the surgeon console can be between the selected instrument and an input device 304 of the surgeon console 400. Suitably, the select signal permits identification of an input device to which the selected instrument is to be operatively coupled. For example, the select signal may comprise an input device identifier for identifying the input device to which the instrument is to be operatively coupled. Suitably the control system 308 is configured to enable control of the selected instrument by the input device 304 identified by the input device identifier. The select signal need not comprise an input device identifier. For example, where one input device selects an instrument which is to be operatively coupled to that input device, the control system can enable operative control between the input device from which the select signal originates and the selected instrument.

The input device 304 is associatable with, or operatively couplable to, one instrument 320 at a time. This association or coupling is, in one example, controlled by the control system 308. The association or coupling may be effected in software control. The input device 304 is suitably associatable with, or operatively couplable to, an instrument when that instrument is associated with the manipulation mode. The control system 308 may be configured, in response to the received select signal, to cause the selected instrument to enter the manipulation mode.

Figure 6:
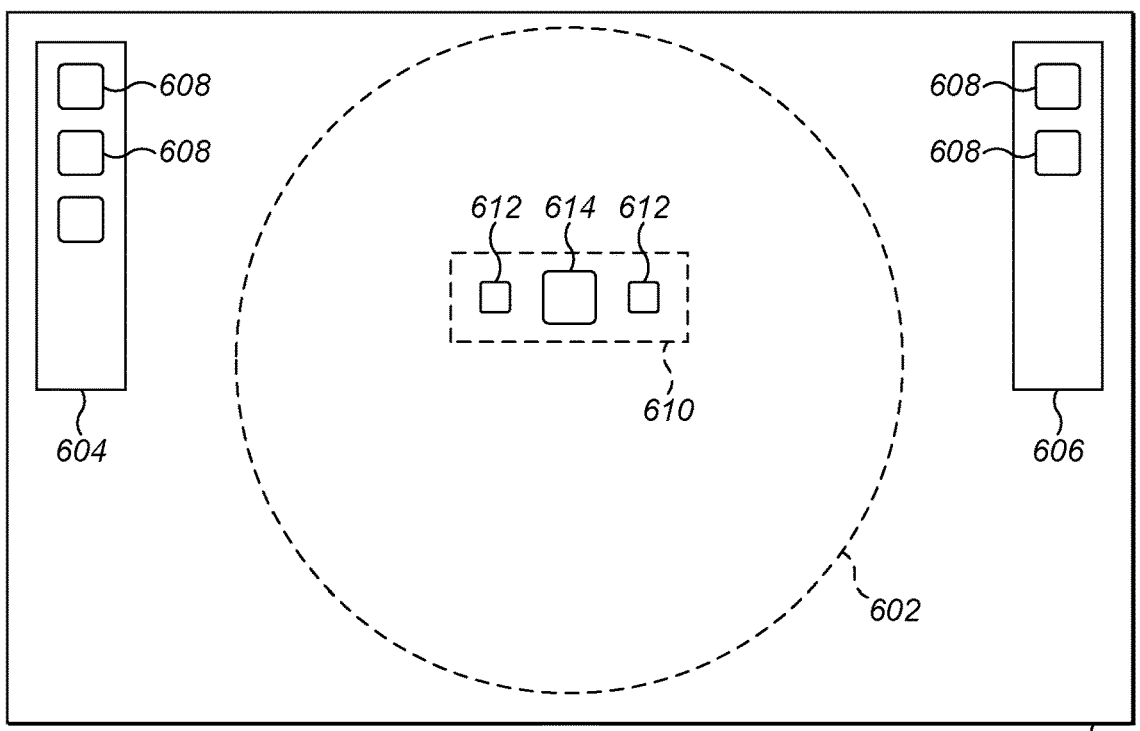
FIG. 6 illustrates an example of a display showing a graphical arrangement of icons.

Reference is now made to FIG. 6, which shows an example of a graphical arrangement of icons. The graphical arrangement of icons is displayed on a display 306. The display 306 comprises a rectangular screen. In other examples screens of other dimensions may be used.

Suitably, the graphical arrangement of icons comprises a list region and a selection region. The list region is a region in which an icon representing one of the plurality of instruments is caused to be displayed, for example prior to the change of mode to the selection mode. The selection region is a region in which an icon representing a selectable instrument of the plurality of instruments is caused to be displayed in the selection mode. Suitably the list region and the selection region are at least partially non-overlapping.

The graphical arrangement of icons is suitably provided on the display device so as to overlay a received image feed, for example an image feed received from a surgical site. This enables a user to view the icons together with the image feed. The graphical arrangement of icons permits the user to identify one or more aspects of the state of the system, for example whether the respective instrument is available or selectable for control, whether the instrument is being controlled, for example whether the instrument is in the manipulation mode, and/or which input device is operatively coupled to the instrument.

In the example illustrated in FIG. 6, the image feed 602 is provided central to the display 306. The image feed is shown as a roughly circular image, but may be of any shape. Typically an image from an imaging device such as an endoscope will be rectangular. Image feeds of other dimensions may be provided. The circular image illustrated in the figures suitably represents a central portion of the image of the surgical site, or that portion of the image of the surgical site that is most important or of most interest. The image, as illustrated in the figures, may be of any suitable shape. The image feed 602 occupies substantially the full height of the display, but in the illustrated example does not occupy the full width of the display. This means that there are regions to either side of the displayed image feed in which graphical representations can be provided without interfering with the surgeon's view of the image feed. These are illustrated in FIG. 6 by box regions 604 and 606. Each of the box regions 604 and 606 suitably corresponds to a respective input device. The box regions need not be shown as boxes on the display, but indicate an extent of a region. In some examples, there may be regions to the top and/or bottom of the displayed image feed in which graphical representations can be provided without interfering with the surgeon's view of the image feed.

One box region 604 is provided to the left of the display and suitably corresponds to a left-hand input device. Another box region 606 is provided to the right of the display and suitably corresponds to a right-hand input device. Each of the box regions contains icons 608 representing instruments that are connected to the robotic system. The left-hand box region 604 suitably contains icons for instruments that are operatively coupled to the left-hand input device, or were most recently coupled to the left-hand input device. The right-hand box region 606 suitably contains icons for instruments that are operatively coupled to the right-hand input device, or were most recently coupled to the right-hand input device.

The list region suitably comprises the box regions 604, 606. The control system 308 is suitably configured to cause icons representing instruments to be displayed in the list region 604, 606 when those instruments are in at least one mode of the group of modes, such as the manipulation mode.

Where the respective input device 304 (or more generally, the surgeon console 400) is operatively coupled to an instrument, one of the icons 608 in the respective box region 604, 606 is suitably differentiated from the remaining icons in that box region to permit identification of the instrument which is being controlled by that input device 304 (or by the surgeon console 400). The instrument that is being controlled can be termed an active instrument. Other instruments, which are not being controlled, can be termed non-active instruments.

Suitably, the system is configured to highlight to the user which of the instruments is the current active instrument by causing the corresponding icon for that instrument to change in at least one of size, position, position in a list of other icons, colour, lighting, background, outline, highlight image and visual effect such as a glow effect. Additionally or alternatively the system may be configured to highlight to the user the active instrument by causing the corresponding icon for that instrument to change from being two-dimensional to being three-dimensional, or from being three-dimensional to being two-dimensional. This can be particularly effective when the image is displayed in three-dimensions, as this can permit the user to more naturally see the correspondence between the representation for the active end effector and the respective end effector as visualised in the image.

Examples of ways of changing the background include causing the icons to be contained in a shape such as a circle or a polygon. The shape containing the icon for the active instrument can be larger than those for the other icons, and/or have a border of a different width. For example, the shape containing the icon for the active instrument suitably has a thicker border than the other shapes. In some examples, the shape containing the icon for the active instrument is different from the shapes containing the other icons. Suitably the shapes containing the other icons are all the same shape. For example, the icon for the active instrument can be contained in a circle and all the other icons can be contained in a square. Use of other shapes or combinations of shapes is possible. In some examples the colour of the backgrounds of the icon for the active instrument and the other icons can be differentiated. For example, the background of the icon for the active instrument can be green, and the background of the other icons can be orange.

In some examples, the icon can be larger for an active instrument than for a non-active instrument. The icon can be indented from the edge of the display (or closer to the edge of the display) for an active instrument compared to the position of an icon for a non-active instrument. The icon for an active instrument can be placed higher or lower in a list, such as a vertical list, or to the right or left in a list, such as a horizontal list, of possible instruments, compared to one or more non-active instruments. Suitably, the list is a vertical list, and the active instrument icon is located at the top of the list. In other examples in which the list of icons is located horizontally and/or towards the bottom of the display, the active instrument icon may similarly be provided closest to the corner of the display (or to another easily determinable feature). This can allow quick identification of the active instrument. Suitably the icons are arranged towards or at the right or left margins of the display, and/or towards or at the upper or lower margins of the display so as to reduce or minimise the interference of the icons with the image feed.

The icon representing an active end effector can be provided in a different colour from the representations of the non-active end effectors, such as in a brighter and/or more distinct colour. In one example, icons representing non-active end effectors are provided in black and white and icons representing active end effectors are provided in full colour.

Figure 12:
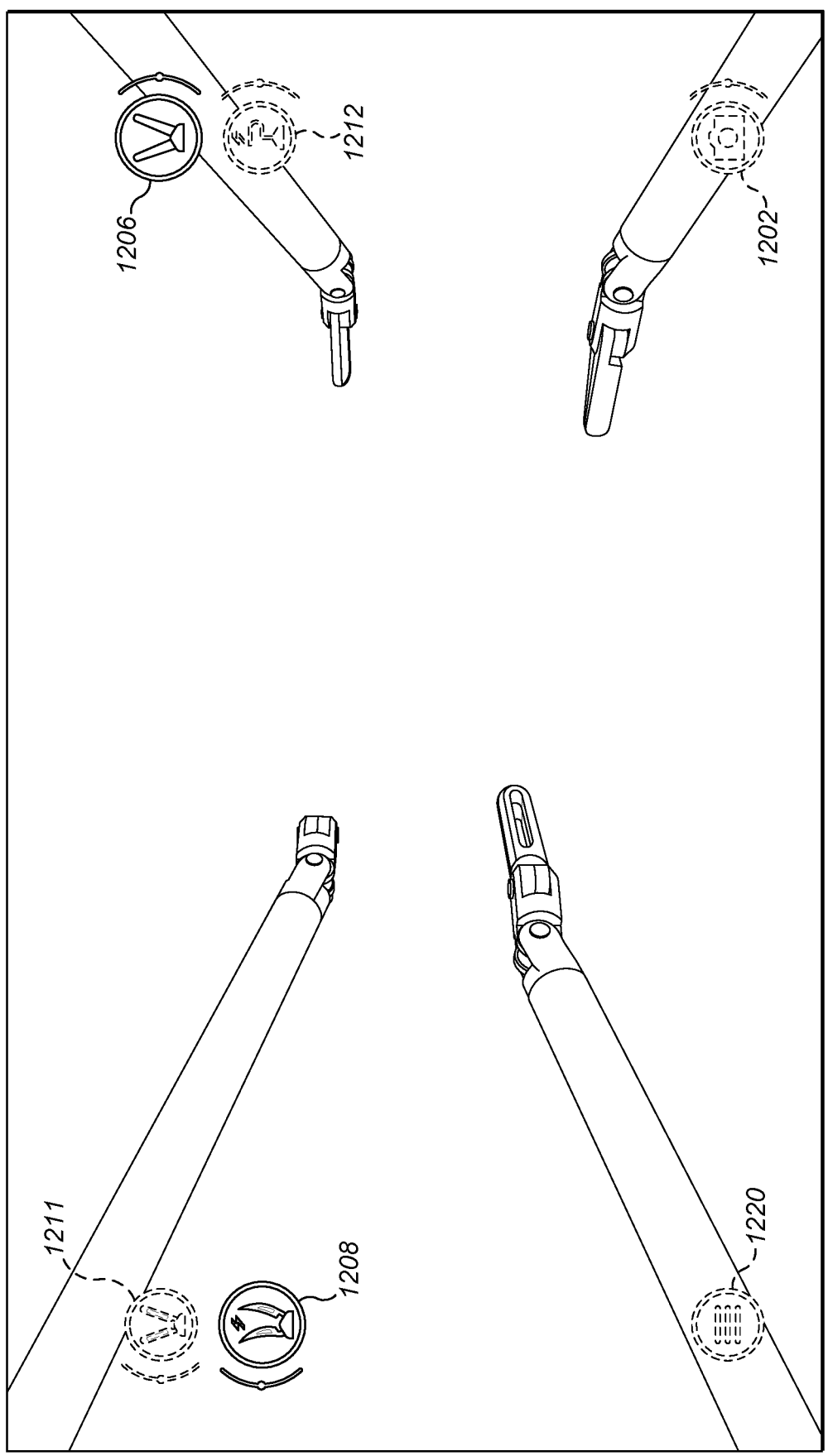
FIG. 12 illustrates another example of a display showing a graphical arrangement of icons.
Figure 13:
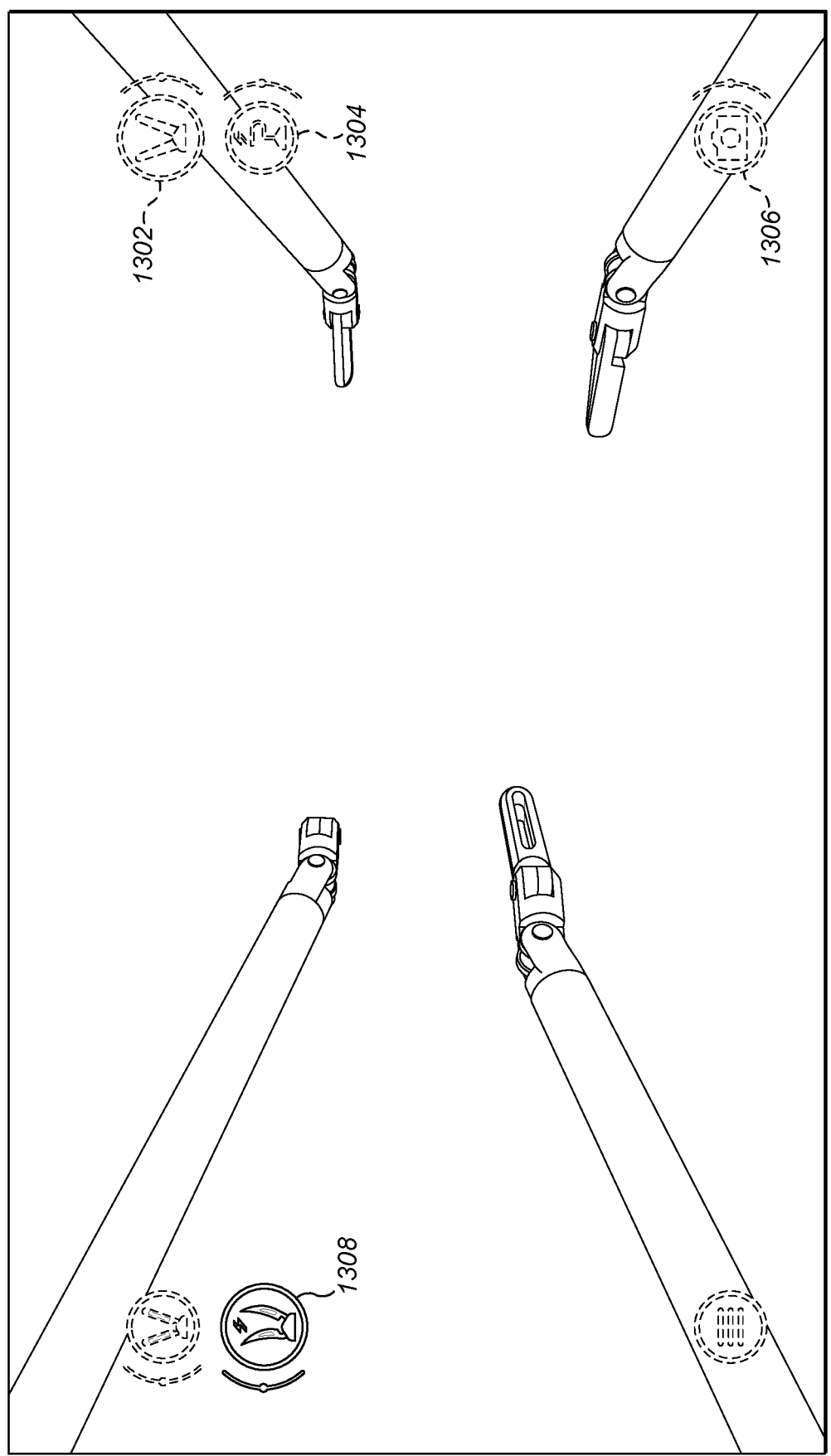
FIG. 13 illustrates another example of a display showing a graphical arrangement of icons.
Figure 14:
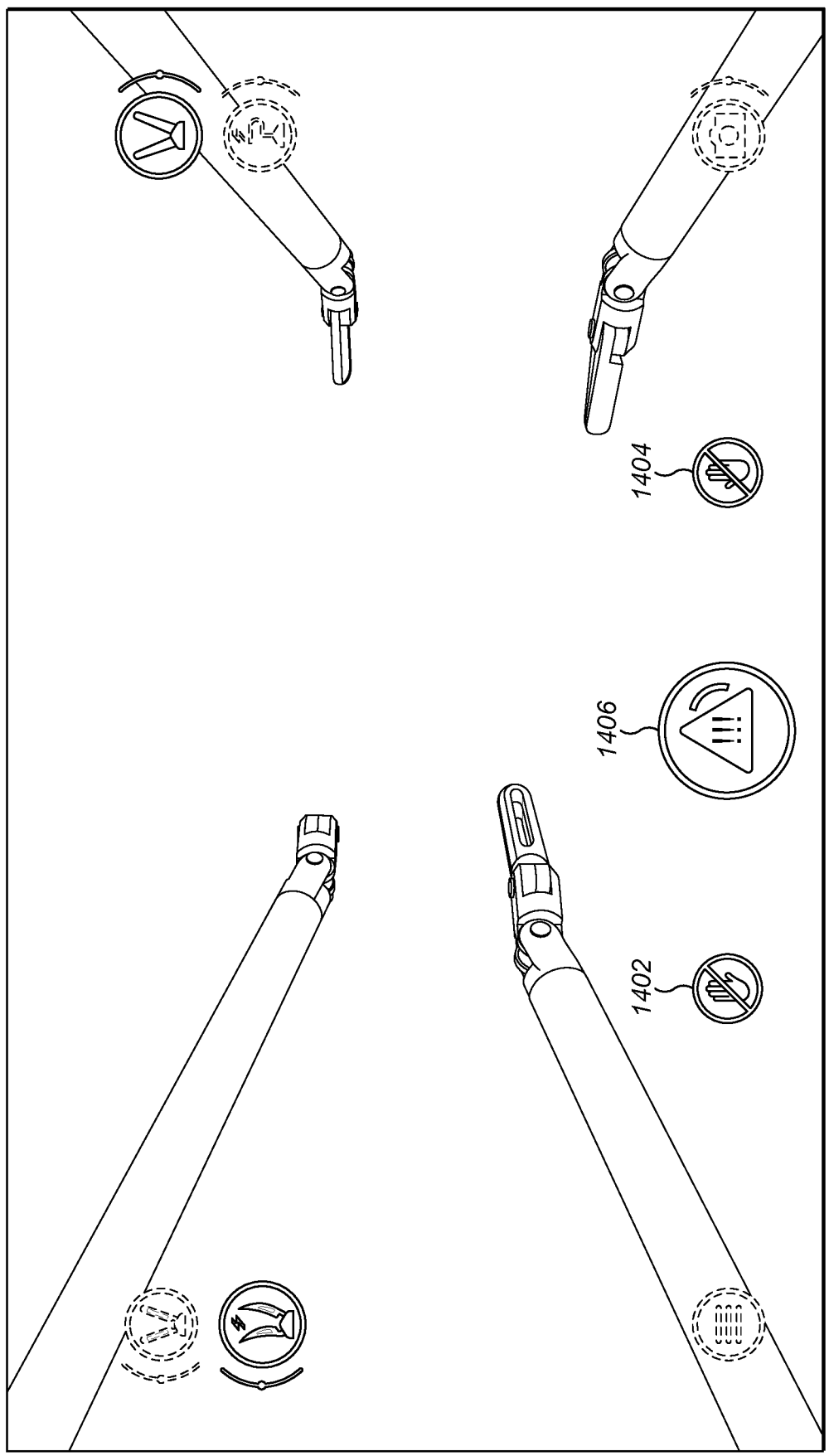
FIG. 14 illustrates another example of a display showing a graphical arrangement of icons.

Differences in transparency of the icons can be used to distinguish between icons representing active end effectors and icons representing non-active end effectors. An icon representing an active end effector can be provided as a relatively less transparent icon, and an icon representing a non-active end effector can be provided as a relatively more transparent icon. For example, an icon representing an active end effector can be provided as a solid icon, and an icon representing a non-active end effector can be provided as a transparent, partly transparent, or greyed out icon. With reference to FIGS. 12 to 14, the relatively more transparent icons are indicated in dotted lines. Whilst the icons on the display can be shown in dotted lines, this need not be the case.

In some examples, combinations of these approaches are possible.

Providing the icons, as shown in the example illustrated in FIG. 6, towards a periphery of the display can mean that when a user such as a surgeon is viewing the display, the icons are displayed in the peripheral vision of the user. There is therefore a risk that the user may need to change their gaze, or change where their attention is directed, in order to properly view the icons and to be able to fully assess the state of the surgical robot. This is due to a significant reduction in visual acuity in a user's peripheral vision. This can be undesirable, especially in surgical robotic contexts where the surgeon's attention is more properly focussed on the surgical site during a surgical procedure. Thus, it is desirable that the system can be operated without relying on a user's peripheral vision and without diverting the user's attention from the surgical site when operating the surgical robot and interacting with the surgeon console.

The graphical arrangement of icons illustrated in FIG. 6 comprises a selection region 610. Suitably, in the selection mode, icons associated with the one or more selectable instruments are caused to be displayed in the selection region 610. Suitably the instrument selection region 610 is non-overlapping with the list region 604, 606, as illustrated in FIG. 6. For example, the instrument selection region 610 is provided at a different portion of the display from the list region 604, 606. This permits easy identification of whether the icons are provided in the list region or the selection region. It also permits the provision of the list region at a location where the icons will not interfere with the surgeon's vision during a surgical procedure, and the provision of the selection region at a location where the icons are easily identifiable by the surgeon without the need to use peripheral vision or to divert attention away from the image of the surgical site.

Suitably, the list region is provided one of at and towards a periphery of the graphical arrangement of icons. The list region is preferably provided towards a periphery of the display, for example so as to be in a region of peripheral vision of a user looking at the central part of the display 306 (such as that part displaying an image feed 602).

Suitably, the graphical arrangement of icons comprises an image region for displaying an image of a surgical site. The image region is provided towards a centre of the graphical arrangement of icons. Suitably, the list region is at least partially non-overlapping with the image region. This can reduce the interference of icons in the list region with the image shown in the image region.

Suitably the selection region 610 is provided towards the centre of the display 306. The selection region 610 may be provided so as to at least partially overlap the image region 602. Thus a user focussing on the image feed will be able to view the selection region without needing to divert their attention away from the image feed. In one example, the control system 308 is configured to cause the selection region 610 to be displayed in the centre of the display 306, as illustrated schematically in FIG. 6.

In such examples, the user is presented with icons 608 in the list region which do not interfere with the user's view of the image feed when in the manipulation mode. In the selection mode, the user is presented with icons 612, 614 in the selection region 610 which can be easily identified by the user so as to permit selection of the desired instrument whilst still viewing the image region 602.

In one example, where the system is in the manipulation mode, an instrument 320 will be operatively coupled to the surgeon console 400, for example by being operatively coupled to an input device 304 of the surgeon console 400. In such an example, the control system 308 is configured to cause the icon 608 for this instrument to be displayed in the list region 604, 606. In another example, where the system is in a setup or startup mode, an instrument 320 may be coupled to the surgeon console 400 but this coupling may not permit operative control of the instrument by the surgeon console. For example, an instrument 320 may be newly coupled to the surgical robot. In this case the instrument may not immediately be operatively couplable to the surgeon console 400. The instrument may be operatively couplable to the surgeon console at a later time, for example after setup checks have been performed. In this example, the control system 308 may be configured to cause the icon for this instrument to be displayed in the list region.

Suitably, the list region comprises a new instrument region in which an icon representing a newly-added instrument is caused to be displayed. Suitably, the new instrument region is provided so as to at least partially overlap the image region. An instrument can be considered to be newly added if it has been added, or coupled, to the surgical robot within a particular timeframe. The particular timeframe may be the preceding 5 seconds, the preceding 30 seconds, the preceding 1 minute or any other timeframe such as a user-selectable timeframe. The user-selectable timeframe is suitably selectable by the surgeon console. The timeframe may be specified in a startup routine for the surgeon console, the surgical robot and/or the instrument. Suitably an instrument is considered to be newly added if it has not been selected for use since being coupled to the surgical robot. Suitably an instrument is considered to be newly added if it has not entered a selection mode since being coupled to the surgical robot.

Figure 7:
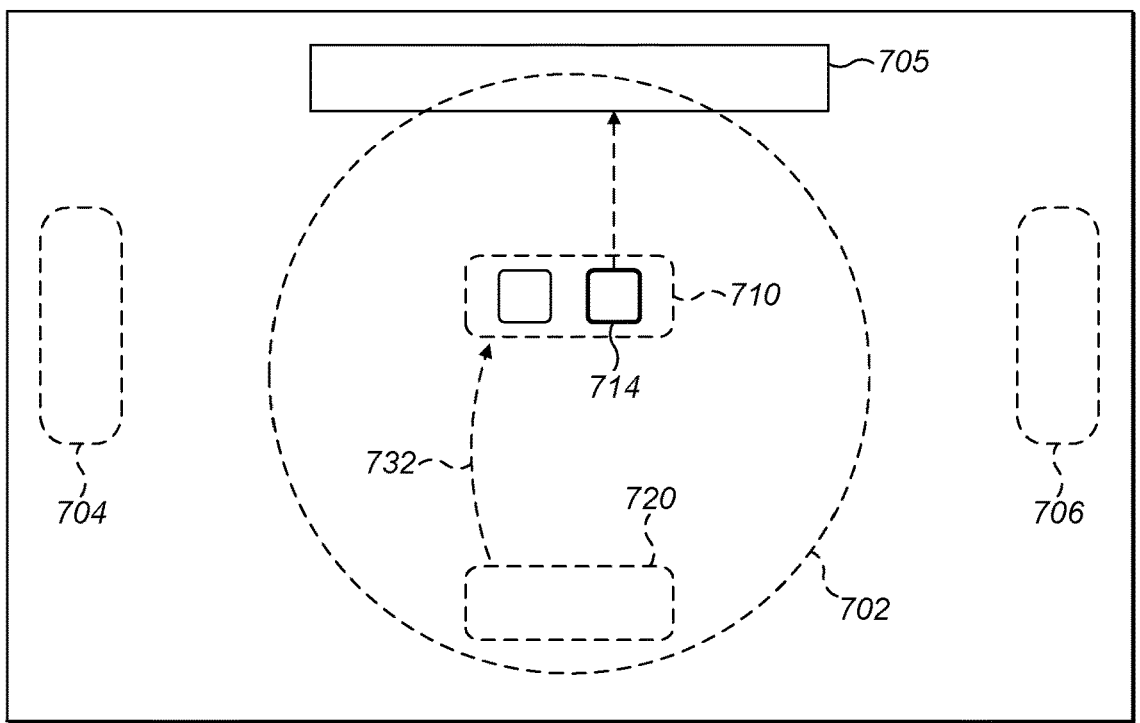
FIG. 7 illustrates another example of a display showing a graphical arrangement of icons.

With reference to the example illustrated in FIG. 7, the control system 308 is configured to provide a new instrument region 720. The control system 308 is configured to cause the icon for the newly added instrument to be displayed in the new instrument region 720. Suitably the new instrument region 720 is non-overlapping with a portion of the list region, for example the portions depicted by reference numbers 704, 706. Suitably the new instrument region 720 is provided one of at and towards a periphery of the display. In the illustrated example the new instrument region 720 is provided to be at least partially overlapping with the image region 702. For example, the new instrument region 720 may be provided at a bottom portion of the image region 702. The provision of the icons in the new instrument region 720 indicates to the user that the associated instruments 320 are available, for example that they are selectable for control by the surgeon console. Causing the icons for these instruments to be displayed in a central portion of the display (rather than a left or right portion of the display) can indicate to the user that the instruments are not (or have not been) associated with any particular input device 304. The display in a central region of these icons can indicate to the user that the associated instruments are not (or have not been) associated with one or other of a left-hand input device and a right-hand input device. The central location of the new instrument region 720 can indicate the 'neutrality' of the relevant instruments, for example with respect to the input devices.

In response to receiving the mode change signal from the surgeon console indicating a change of mode to the selection mode, the control system 308 is suitably configured to modify the graphical arrangement of icons so as to cause the icons associated with selectable instruments to be displayed in the selection region 610, 710 instead of in the list region 604, 606, 704, 706, 720. This modification indicates to the user which of the instruments are selectable. Further, since the icons for the selectable instruments are caused to be displayed in the selection region 710 which is suitably provided overlapping the image region 702, the user need not look away from the image region to be able to select an instrument 320. Thus, a user such as a surgeon can maintain their focus on the image feed during an instrument selection process. This can help reduce the risks associated with the surgeon's attention being diverted from the image feed of a surgical site during a surgical procedure.

Suitably the new instrument region 720 overlaps with the selection region 710. Thus, on the modification of the graphical arrangement of icons by the control system to display icons associated with selectable instruments in the selection region instead of in the new instrument region, there need not be a movement of the respective icons. In one example, a particular icon representing a selectable instrument is caused to be displayed in a particular location on the display in the new instrument region. On entering the selection mode, the control system can cause that particular icon to be associated with the selection region in place of the new instrument region. The change in the region in which that icon is displayed (or the change in the region with which that icons is associated) need not result in a change in the location on the display where that icon is displayed.

Icons representing non-selectable instruments may remain in their previous location in the graphical arrangement of icons, for example in the list region, such as in the new instrument region.

Suitably, the control system 308 is configured, in response to receiving the mode change signal, to cause a transition of the icon representing the selectable instrument to the selection region 710 to indicate that the respective instrument is selectable. The transition of the icon may be from the list region to the selection region.

The transition may, for example, comprise a gradual or smooth transition. The transition may be a continuous transition. The transition may be animated. An example of such a transition is the icon moving across the display towards the selection region 710. This can assist the user to understand which instruments are available for selection. Hence, if icons from a right-hand list 706 transition to the selection region 720 the user can appreciate, for example, that instruments which have been associated with a right-hand input device are selectable.

Figure 8:
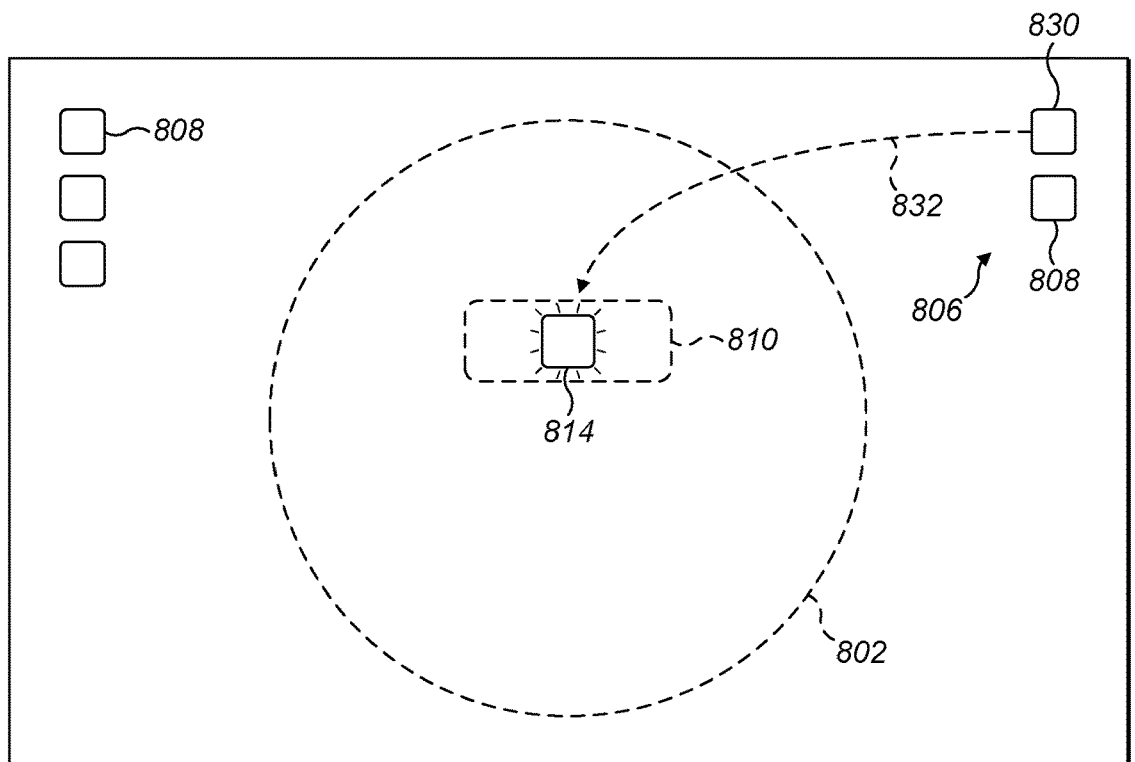
FIG. 8 illustrates another example of a display showing a graphical arrangement of icons.

This is schematically illustrated in FIG. 8. FIG. 8 illustrates a display 306 on which the control system 308 causes to be displayed an image region 802 for providing a view of an image feed such as from a surgical site. Icons 808 are provided in a left-hand list region and a right-hand list region 806. On changing to the selection mode, an icon 830, which is associated with a selectable instrument, transitions from the right-hand list region 806 to the selection region 810. This transitioning is schematically illustrated by a dashed line 832. Similarly, with reference to FIG. 7, icons in a new instrument region 720 can be caused to transition to the selection region 710 (as schematically illustrated in FIG. 7 by a dashed line 732). This allows the user to appreciate that new instruments which have not already been used and/or selected are selectable. Such transitions can provide intuitive indications to the user about which instruments are selectable.

Suitably, the control system 308 is configured to receive an input signal from each of a plurality of input devices of the surgeon console. The graphical arrangement of icons suitably comprises a plurality of selection regions with each input device being associated with a respective one of the plurality of selection regions. For example, the graphical arrangement of icons may comprise a left-hand selection region associated with a left-hand input device and a right-hand selection region associated with a right-hand input device. Suitably, the control system is configured, in response to receiving the mode change signal, to cause icons representing instruments selectable by each input device to be displayed in the respective selection region for that input device. For example, on receiving the mode change signal, the control system 308 is configured to cause icons representing instruments selectable by a left-hand input device to be displayed in the left-hand selection region and to cause icons representing instruments selectable by a right-hand input device to be displayed in the right-hand selection region.

It is noted that there may be icons that can be caused to be displayed in each of the respective selection regions. For example, it is possible for an instrument to be controllable by either of a left-hand input device and a right-hand input device. In one example, the control system 308 is configured to cause the icon representing such an instrument to be displayed in each of the respective selection regions. On selection in one of the selection regions, the icon will no longer be selectable in the other selection region or selection regions. This can be indicated to a user by greying out the icon, removing the icon from the other selection region or selection regions, or in any other suitable way.

For example, transparency of the icon can indicate that it is no longer selectable. I.e. the icon may be solid when it is selectable, and at least partly transparent when it is no longer selectable.

Suitably, the control system is configured such that the modification to the graphical arrangement of icons permitting identification of the selectable instruments comprises one or more of changing the colour of an icon, changing the size of the icon, changing the background of the icon, changing the icon from a two-dimensional icon to a three-dimensional icon, changing the icon from a three-dimensional icon to a two-dimensional icon, causing the icon to flash, and causing the icon to flash with a modified frequency. Any convenient way of distinguishing the icons, for example as described above in the context of distinguishing icons for active instruments, can be used. Suitably icons for selectable instruments are distinguished in a different way to icons for active instruments. Such a modification permits easy identification by a user of the selectable instrument.

In some examples, the control system 308 is configured to receive an image signal representative of an image from a surgical site, and to cause the display of the image in the image region. The displayed image suitably comprises an instrument image of an instrument at the surgical site. The control system is suitably configured to modify the instrument image in response to receiving the mode change signal. This permits easy identification of the instrument corresponding to the modified instrument image.

For example, instrument images corresponding to selectable instruments can be modified. Thus, a user at the surgeon console can identify selectable instruments whilst viewing the image of the surgical site, without needing to divert their attention. This modification of the instrument image or instrument images can be made in addition to the highlighting and/or transitioning of icons or as an alternative to the highlighting and/or transitioning of icons.

The control system 308 is suitably configured to modify the instrument image by at least one of overlaying graphics on the image region, modifying graphics overlaid on the image region, and removing graphics overlaid on the image region. In one example, a 'false colour' can be applied graphically to the instrument image by overlaying the colour over at least a portion of the displayed instrument image. The colour overlay need not be applied continuously to the instrument image. In one example, the colour overlay is applied in response to the user operating a user control. The user may operate the same control again, or operate another control, to cause the colour overlay to disappear. The colour overlay may automatically disappear after a particular time period has elapsed. The particular time period may be selectable, such as by a user. The particular time period can, for example, be 2 seconds, 5 seconds, 10 seconds, or any other suitable time period.

The portion of the instrument image over which the colour overlay is applied may be the shaft (or a portion thereof) of the instrument (to the extent that this is visible in the image region). This permits the end-effector of the instrument to be seen without any overlay. This can help increase the clarity with which the end-effector is viewed by the surgeon.

Suitably, the control system 308 is configured to modify the instrument image to correspond to the modification to the graphical arrangement of icons permitting identification of the selectable instruments. This permits the user to identify the selectable instruments from either or both of the icons and the instrument images. This enables the user to maintain focus on the most appropriate part of the display, according to the situation.

In some examples, the control system 308 is configured, in response to receiving the select signal, to cause the icon associated with the selected instrument to be displayed in the list region 604, 606, 704, 706, 806. For example, the control system 308 may be configured to cause the relevant icon to be displayed in the list region associated with the respective input device.

In at least some examples, the control system 308 is configured to cause the selected icon to transition from the selection region 610, 710, 810 to the list region. For example, the transition can be an animated transition, such as the icon moving across the display. The transition can permit intuitive understanding by the user of the selection of the associated instrument. The transition can permit intuitive understanding by the user of the operative coupling of the associated instrument to a particular input device. For example, where the icon transitions to the left, such as to a list region associated with a left-hand input device, the user can readily appreciate that the associated instrument is then operatively coupled to the left-hand input device.

Suitably at least one of the list region, the selection region and the new instrument region comprises a border around at least a portion of its periphery. Suitably, the control system is configured to modify the border in response to receiving the mode change signal to permit identification of the change of mode. Suitably the border is spaced from the border of the display. The modification of the border can be made in a bold, bright and/or flashing colour. This can enable the change to be noticeable even if the border, such as a border of the list region, is displayed in a region which will be in a surgeon's peripheral vision when concentrating on an image of a surgical site shown on the display. This can assist in communicating the state of the robotic system to the surgeon.

Suitably the control system is configured to modify the border in dependence on an aspect of the state of the robotic system. For example, the border can comprise a colour bar, and the control system can be configured to modify the colour bar to indicate a status of an electrosurgical tool. For example, the colour bar can indicate the power state and/or temperature of an electrosurgical tool. This can enable the surgeon to distinguish between an electrosurgical tool in a 'cut' state from one in a 'coagulate' state. For example a blue border can be used to indicate one of the cut state and the coagulate state, and a yellow border can be used to indicate the other of the cut state and the coagulate state.

Suitably an icon comprises an icon border. The icon border can be coloured and/or hatched, and so on, to indicate an aspect of a status of the respective instrument and/or end effector. For example, an electrosurgical tool can have a cut mode and a coagulate mode. An icon representing such an electrosurgical tool can comprise a coloured icon border. The icon border is suitably able to permit distinguishing between these modes. For example, a yellow icon border can indicate that the instrument is in a cut mode, and a blue icon border can indicate that the instrument is in a coagulate mode. In some examples, the border may be a third colour, for example white, when the instrument is in neither of the cut or coagulate modes. This may be because the instrument is switched off (or has not yet been switched on) and/or because there is no power to the electrosurgical end effector.

The list region need not be provided towards a side periphery of the display in all examples. Referring to FIG. 7, in one example, the list region 705 is provided towards an upper portion of the display 306. In a similar manner to that described above, the control system 308 is suitably configured to cause icons in the list region 705 that are associated with selectable instruments to transition to the selection region 710 in response to receiving the mode change signal indicating a change of mode to the selection mode.

An example of the operation of the control system will now be briefly described. In this example, before first use, i.e. in an initial setup phase, all icons for instruments coupled to the system will appear in the selection region 710, which is suitably caused to be displayed in the centre of a display. A surgeon at the surgeon console may then choose which instruments they wish to put into a list of instruments associated with a left-hand input device and which instruments they wish to put into a list of instruments associated with a right-hand input device.

A control at the left-hand input device, for example a joystick control, is suitably able to select icons from the selection region. An indicator associated with the left-hand input device, for example an arrow (or triangle) to the left of an icon and pointing to the right, can be moved by the control at the left-hand input device. A button, for example a button at the left-hand input device, can be operated to select the icon. A control at the right-hand input device, for example a joystick control, is suitably able to select icons from the selection region. An indicator associated with the right-hand input device, for example an arrow (or triangle) to the right of an icon and pointing to the left, can be moved by the control at the right-hand input device. A button, for example a button at the right-hand input device, can be operated to select the icon.

Once selected, the icons suitably move to the list region 704, 706. Icons selected by the left-hand input device suitably move to the portion of the list region 704 towards the left of the display. Icons selected by the right-hand input device suitably move to the portion of the list region 706 towards the right of the display. The first active instrument can be selected by the respective input devices in a similar manner. The icon for the selected active instrument is suitably then highlighted in the list of icons in the list region 704, 706. For example, the icon for the active instrument may get bigger and/or move to the top of the list.

The control system is suitably configured to respond to signals from the input devices so as to permit the input devices to be independently operable. I.e. the surgeon is able to select icons using both input devices at once, or sequentially.

Respective active icons (associated with active instruments) will then be associated with each input device. On entering the selection mode, the control system is suitably configured to permit selection by one input device of any instrument except the instrument that is operatively coupled to another input device (i.e. any icon or instrument may be selected except an active icon or instrument). Suitably the instrument change process, whereby an input device is operable to select another icon, occurs sequentially for each input device. In an example, a particular icon can be initially moved by the surgeon to the portion of the list region 704 associated with the left-hand input device, but not selected as the active icon. Then, on entering the selection mode, the right-hand input device is able to select that particular icon. On selection, that particular icon suitably moves to the portion of the list region associated with the right-hand input device 706. That particular icon can be highlighted to show that it is an active icon, i.e. that that icon is associated with an active instrument.

The control system is suitably configured so that an icon for a new instrument added to the system after the initial phase (in which the surgeon allocates icons to the left or right portions of the list region 704, 706) is caused to be displayed centrally in the display, for example in one of the portion of the list region 705 towards an upper portion of the display and the new instrument region 720. From either region, the control system is suitably configured to permit the surgeon to allocate the icon to either of the left or right portions of the list region 704, 706, in a similar manner to that described above.

Figure 10:
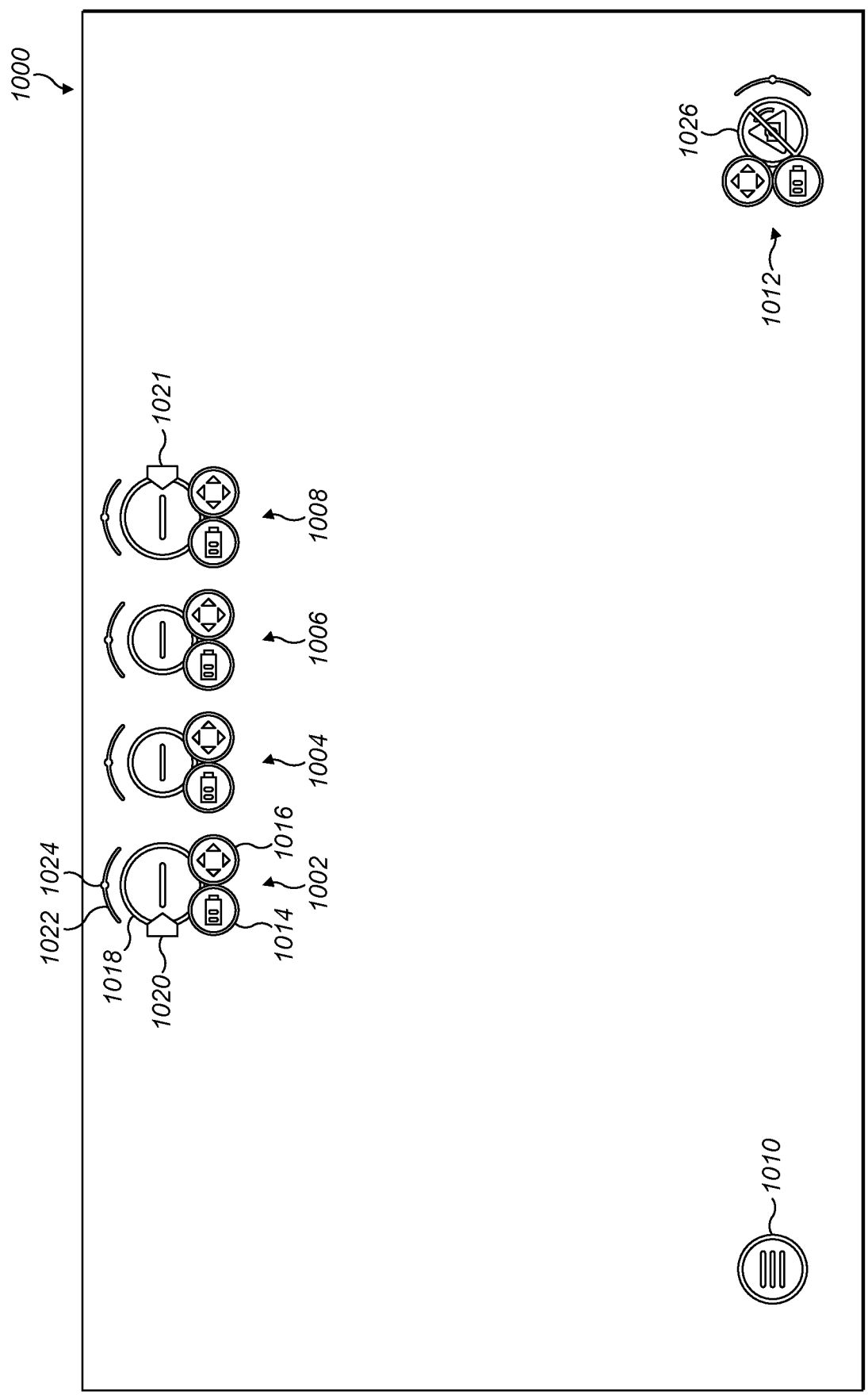
FIG. 10 illustrates another example of a display showing a graphical arrangement of icons.

Further examples of graphical arrangements of icons will now be described. Referring to FIG. 10, a graphical arrangement of icons 1000 comprises icons 1002, 1004, 1006, 1008 which represent each of four robotic arms coupled to the robotic system. These icons are provided towards an upper central portion of the display.

Suitably the icons are associated with respective arms coupled to the system. Suitably a colour is used to associate an icon with an arm. For example, the background of an icon can be, or can comprise, a colour which is associated with a particular arm. For example, where four arms are provided for the coupling of four instruments, the arms can each have a different colour associated with the arm, such as yellow, blue, red and purple. The background of the respective icons can be one of these four colours. Of course, any colour and/or combination of colours can be used. The colours and/or combination of colours are used to enable the icons/ arms to be distinguished from one another.

The graphical arrangement of icons 1000 comprises a menu icon 1010, which in this example is provided in a lower left portion of the display. The graphical arrangement of icons comprises an imaging device icon 1012, which in this example is provided in a lower right portion of the display. Suitably the menu icon 1010 and the imaging device icon 1012 are provided in different regions of the display from one another.

The menu icon 1010 can be used to bring up or access different options. Suitably all options are accessible through the menu icon. For example, selecting the menu icon can bring up a list or table of options. Sub-options may be accessible through one or more of these menu options. Such menu structures will be well known to the skilled person. The menu is suitably navigated using one or more control at the input devices. Suitably the thumb stick of at least one of the left-hand input device and the right-hand input device is used to navigate the menu.

At least one icon of the graphical arrangement of icons can comprise a plurality of sub-icons. The sub-icons can form a cluster of icons. Referring to FIG. 10, the icons 1002, 1004, 1006, 1008 and the imaging device icon 1012 comprise a cluster of three circular sub-icons. Each of the sub-icons suitably provides a status associated with the respective arm. For example, each sub-icon suitably provides a status of a different aspect of the instrument or arm which that icon represents. One sub-icon may be distinguished from the rest of the plurality of sub-icons. The one sub-icon is suitably distinguished by being larger than the rest of the plurality of sub-icons. The one sub-icon can be distinguished from the other sub-icons in any convenient way, for example as described herein, such as by being a different colour, shape, transparency, intensity, by flashing, and so on.

Suitably the cluster of icons is visible during at least one of the setup mode, the selection mode and the new instrument mode. Suitably, during normal operation or control of an instrument, the respective icons comprise a single icon. Suitably the sub-icon that is distinguished from the other sub-icons when the cluster of sub-icons is visible is the icon that is displayed during normal operation. Suitably this sub-icon indicates the instrument type. Thus, in normal operation, the icon that is displayed will be an icon that indicates the particular instrument and/or end effector that is operatively coupled to the robot arm.

In the example illustrated in FIG. 10, the cluster of icons comprises three sub-icons. One sub-icon comprises a battery icon 1014. This indicates the battery level of the respective arm. It may additionally or alternatively indicate an amount of power remaining, whether or not the arm is coupled to a power source, and/or whether or not the arm battery is charging.

Another sub-icon comprises an orientation icon 1016. The orientation icon 1016 may be useful where robot arms can be mounted in more than one orientation. The orientation may be relative to a frame of reference such as an operating room or a patient bed. Generally, the orientation icon 1016 can comprise a number of directional indicators, such as arrows, that corresponds to the number of possible directions that the arms can face (or orientations in which the arms can be provided). The number of possible directions or orientations suitably relates to a number of possible valid directions or orientations. There is suitably a number of directions or orientations in which the arms can be validly provided for use during a procedure. In the illustrated example, there are four equally spaced-apart valid directions or orientations. In this example, the orientation icon 1016 comprises four directional indicators. In some examples, these four orientations correspond to the arms being provided at the left, right, head and foot of the bed. For example, an arm provided at the left of the bed can be said to be pointing to the right, an arm provided at the right of the bed can be said to be pointing to the left, an arm provided at the head of the bed can be said to be pointing down, and an arm provided at the foot of the bed can be said to be pointing up.

In a configuration where two robot arms are mounted or provided to one side of a patient bed, and two robot arms are mounted to the opposite side of the patient bed, the orientation icons 1016 for two of the arm icons will indicate, for example by the right arrow in the orientation icon 1016 being highlighted, or being the only arrow displayed, that these arms face to the right. The orientation icons 1016 for the other two arm icons will indicate, for example by the left arrow in the orientation icon 1016 being highlighted, or being the only arrow displayed, that these arms face to the left.

The orientation of an arm can be determined automatically when it is mounted into a receiving mount, where the location and/or orientation of that receiving mount is known. The orientation of an arm can be selected by a user. This selection can be carried out before the arm is mounted into the receiving mount (for example, where the user selects where the arm is to be located) or after mounting into the receiving mount (for example, where this is not done automatically). The orientation can be selected, for example, by using a control input at an input device, such as a thumb stick, and/or by using a control input such as a button at the arm and/or receiving mount. In some examples the control input can comprise a plurality of buttons arranged in a layout akin to that of the directional indicators illustrated in the orientation icon 1016.

The orientation icon 1016 of each cluster of icons permits a user, such as a surgeon, to know which arm faces in which direction. This can assist in mounting instruments to the correct arms.

Referring again to FIG. 10, the larger sub-icon 1018 for each of the icons 1002, 1004, 1006, 1008 illustrates a horizontal line. In other examples the larger sub-icon can be blank or empty. This indicates that there is no instrument coupled to the respective arms. The graphical arrangement of icons in FIG. 10 illustrates the situation where four arms are coupled to the system, but no instruments have yet been coupled to any of those arms. This could, for example, be illustrative of a setup phase. Suitably, on coupling an instrument to an arm, the larger sub-icon 1018 will comprise an indication of that instrument.

Two of the icons 1002, 1008 comprise arrows: the left-most icon 1002 comprises an arrow 1020 pointing to the right and the right-most icon 1008 comprises an arrow 1021 pointing to the left. As discussed above, these arrows 1020, 1021 indicate that the system is in a selection mode, where the user is able to select an arm for operative coupling to an input device (such as one of a left-hand input device and a right-hand input device).

Suitably, the user can allocate an arm for one of left-hand control and right-hand control even where no instrument is attached to that arm. Suitably the control system permits instruments to be coupled to arms simultaneously with arm selection by the user.

Further, the orientation icon 1016 indicates that an orientation of the respective arms has not yet been selected or determined.

Each of the four icons 1002, 1004, 1006, 1008 comprises an arc 1022 above the respective icons. The arc comprises a marker 1024. The arc indicates the current position in the rotational range of the instrument and/or arm (or of one or more joints of the instrument and/or arm). For example, the location of the marker on the arc can indicate the rotational position of a terminal joint of the instrument. The joint may have a range of ±360 degrees, i.e. two complete revolutions. The marker can be provided at one end of the arc, for example the left-most end, to indicate that the joint is rotated to −360 degrees. The marker can be provided at the other end of the arc, for example the right-most end, to indicate that the joint is rotated to +360 degrees. As illustrated in FIG. 10, each of the markers 1024 indicate that the respective arms are mid-way through the rotational range.

The imaging device icon 1012 comprises a cluster of icons. As illustrated in FIG. 10, the imaging device icon 1012 also comprises a battery icon and an orientation icon. The larger, or main, sub-icon 1026 provides an indication of the imaging device, such as the endoscope. In the illustrated example, there is a warning triangle, indicating that the endoscope is not present, and/or is not operatively controllable. The display of this warning is not necessary in all examples. The absence of an image on the display can also be indicative of the absence of (or a problem with) the imaging device.

It is possible to use the present system with a manual laparoscope. For example the laparoscope can be removed from the robot arm and manipulated manually. In such situations, the imaging device icon can indicate that the imaging device is not available for control using the surgeon console (i.e. the laparoscope may not be robotically controllable when it is being used manually).

Suitably, at least one of the menu icon 1010 and the imaging device icon 1012 are always displayed in the graphical arrangement of icons. Suitably, at least one of the menu icon 1010 and the imaging device icon 1012 are always displayed in the same location in the graphical arrangement of icons.

In some examples, the sub-icons are not limited to indicating battery and orientation information. In some examples, the sub-icons suitably indicate at least one of: battery status, orientation status, the mode the arm is in, a warning condition, a request for user action, and so on.

The sub-icons can appear when desired by a user, for example by operation of a control to make the sub-icons visible. The sub-icons can appear in dependence on the mode of the system. For example, the cluster of icons, i.e. displaying the sub-icons, can appear in the selection mode. At least one sub-icon can appear if required, for example in a warning condition or when there is a request for a user action. Suitably the control system determines when the sub-icons appear. Suitably the control system is configured to make this determination in dependence on at least one of the status of the respective arm and/or of the status of an instrument coupled to that arm, a control signal from the surgeon console and a control signal from the surgical robot. Suitably the control system is configured to cause a warning related to the instrument to appear in the main sub-icon, i.e. the sub-icon displayed during normal operation. Suitably the warning replaces the indication of the instrument type in the main sub-icon (or in the single displayed icon).

Suitably a region of the graphical arrangement of icons at the central lower portion of the display is used for icons relating to the system itself, for example the system as a whole, rather than one of the arms. The control system is suitably configured to cause the display of one or more icons and/or system status or details relating to the system in the system region. The control system is suitably arranged to cause the icons and/or system status or details to be displayed at system start-up, at predetermined points in a procedure, at completion of a procedure, on system shutdown and/or on request, for example from the surgeon console. This is discussed more below with reference to FIG. 14.

Figure 11:
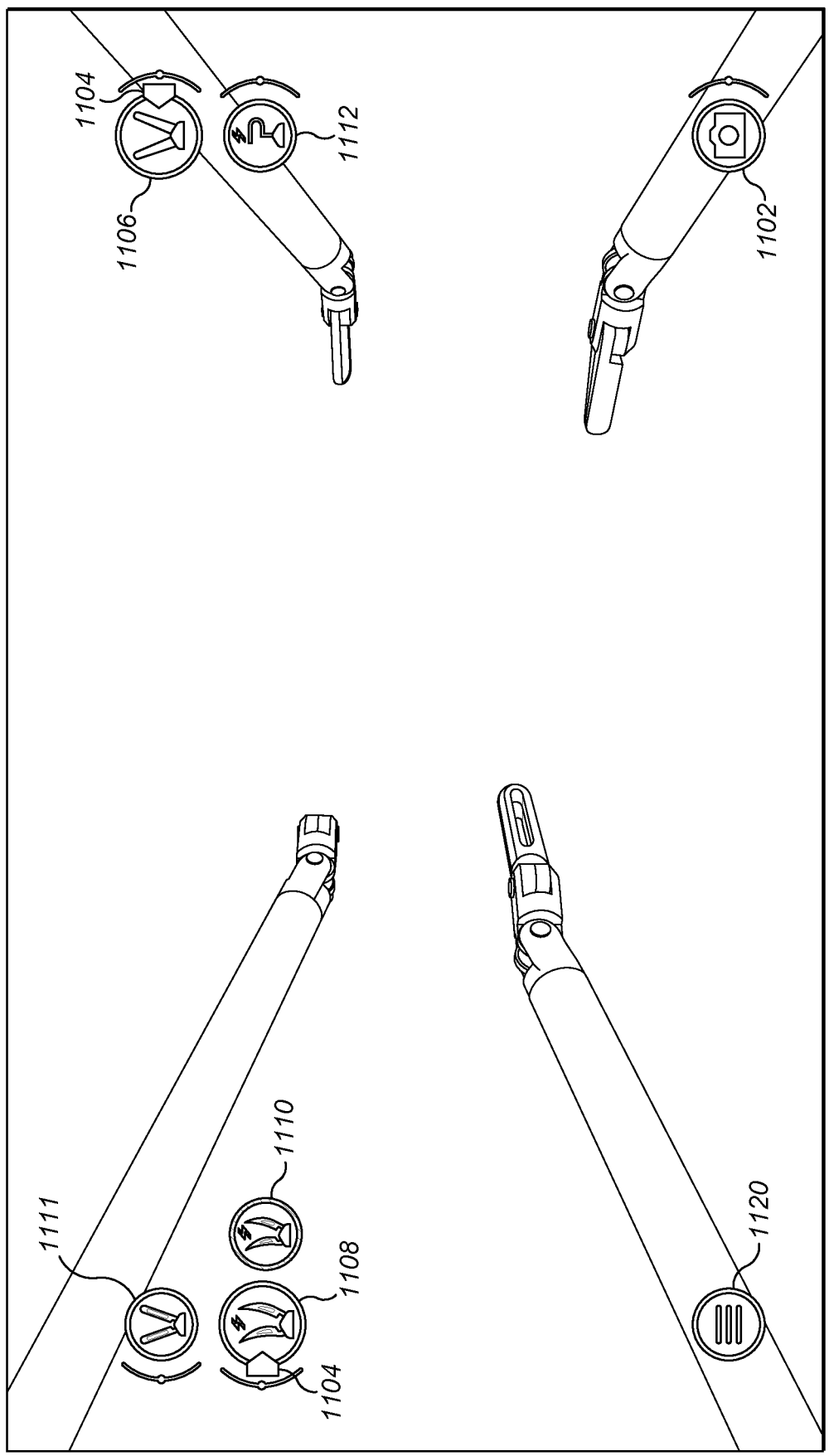
FIG. 11 illustrates another example of a display showing a graphical arrangement of icons.

FIG. 11 illustrates a graphical arrangement of icons where instruments are coupled to the system. Four arms are provided (an additional arm is suitably provided for coupling to an imaging device such as an endoscope), each of which is coupled to an instrument. Icons representing two of the instruments are provided towards the left of the display, and icons representing the remaining two of the instruments are provided towards the right of the display. Icons representing electrosurgical instruments (indicated by the presence of a 'lightning bolt' in the icons) are provided, one to each side of the display.

A camera is shown in the imaging device icon 1102, indicating that an imaging device is coupled to the system.

FIG. 11 illustrates a system in the selection mode. All icons are shown as solid icons. This indicates that all icons are selectable by a user. The imaging device is selectable. For example the imaging device can be selected by a cursor. In this way, the imaging device can be controlled without needing to control an instrument. The imaging device is selectable by both input devices at the same time.

Arrows 1104 indicate the icons that are to be selected by the right-hand and left-hand input devices. The arrow associated with the right-hand input device, i.e. the arrow pointing to the left, highlights a gripper tool 1106. The arrow associated with the left-hand input device, i.e. the arrow pointing to the right, highlights an electrosurgical tool 1108.

Suitably, when an instrument that has additional options is highlighted by a selection arrow, the additional options appear for selection. Here, the electrosurgical tool, such as a bipolar electrosurgical tool, has a cut mode and a coagulate mode. The cut mode is indicated by the icon 1108 towards the left (in the illustrated example). This icon suitably has a yellow border or periphery (more generally, at least a portion of the icon can be coloured yellow). The coagulate mode is indicated by the icon 1110 towards the right (again, in the illustrated example). This icon suitably has a blue border or periphery (more generally, at least a portion of the icon can be coloured blue). The border may alternatively or additionally be distinguished by hatching or in any other convenient way. The currently-selected mode or option can be indicated by the relevant icon being larger than the icons for the other modes or options. Other ways of highlighting the selected icon, such as those described herein, could be used in addition or alternatively. The arrow can be moved between the selected icon, for example the larger icon, and the non-selected icon or icons, for example the smaller icon or icons, as desired. A selection operation, such as at the respective input device, can cause the highlighted or selected option to become or remain as the current option. The icons representing the available modes or options can be ordered by the control system, for example to indicate the most recently used, the last used, the most frequently used, a default, and/or a user's preference from the available modes or options.

On selection of the gripper tool by the right-hand input device, the respective icon 1106 is caused to be distinguished from the other icons, to indicate that the gripper tool has been selected. As illustrated in FIG. 12, the icon 1206 for this tool is larger than the icon 1111 for the other tool. The icon 1206 for the selected tool is illustrated in a solid colour. The icon 1112 representing the other instrument which was selectable by that input device becomes greyed out, or partly transparent. This can indicate that it is no longer selectable. This is illustrated in FIG. 12 at 1212.

On selection of the cut mode of the electrosurgical tool by the left-hand input device, the respective icon 1108 is caused to be distinguished from the other icons, to indicate that this tool has been selected. As illustrated in FIG. 12, the icon 1208 for this tool is larger than the icon 1211 for the other tool. The icons relating to the non-selected options or modes associated with the selected tool, here representing the coagulate mode, disappear. As an alternative to the icons representing the non-selected options disappearing, they may be arranged to be displayed as if 'underneath' the selected icon, and at least partly protruding from underneath that icon. The icon 1208 for the selected tool is illustrated in a solid colour. The icon 1111 representing the other instrument which was selectable by that input device becomes greyed out, or partly transparent. This can indicate that it is no longer selectable. This is illustrated in FIG. 12 at 1211.

In the example illustrated in FIGS. 11 and 12, the menu icon 1120 and the imaging device icon 1102 are shown in solid colour in FIG. 11 to indicate that they are selectable. These icons 1202, 1220 are shown to be partly transparent in FIG. 12 to indicate that they are not selectable.

In some example configurations, the imaging device, such as an endoscope, is controllable by control inputs on both of the left-hand input device and the right-hand input device. For example, a thumb stick on the left-hand input device can control zoom and/or roll, and a thumb stick on the right-hand input device can control panning, or movements of the endoscope. These controls can be the other way round in some examples.

Suitably, in the selection mode, the thumb sticks of the input devices are used to select the instrument (and/or an option or mode associated with the instrument, for example in the case of an electrosurgical tool, whether the tool is to be used in the cut or coagulate mode). Thus, in these examples, the thumb sticks are not available, in the selection mode, to control the imaging device. Thus, in these examples, the imaging device is not user-controllable when the system is in the selection mode. In some examples, the imaging device can remain partly controllable. For example, where the right-hand input device enters a selection mode, and the left-hand input device remains operably coupled to an instrument, the left-hand input device is suitably still able to control the imaging device. In the example above, the left-hand input device is used to control the zoom and/or roll of the imaging device. Hence, this control of the imaging device is still possible during instrument selection using the right-hand input device. The same can be true in reverse: where the left-hand input device is in the selection mode, the right-hand input device is suitably still able to control the panning of the imaging device. As mentioned, the control effected by each thumb stick can be selected as desired.

In other examples, the control system is configured such that the imaging device is not controllable by either of the input devices when either of the input devices is in the selection mode. This can avoid confusion, or inadvertent operation of the imaging device. Similarly, when the menu is being accessed, the menu can be navigated by at least one of the thumb sticks. Suitably, the control system is therefore configured so that at least one of the thumb sticks controls the menu navigation, and not the imaging device. Suitably, where only one thumb stick is used to navigate the menu, the other thumb stick does not permit control of the imaging device. This can avoid inadvertent operation of the imaging device when navigating the menu.

FIG. 13 illustrates an example of a graphical arrangement of icons in which a clutch associated with the right-hand input controller is active or engaged. When the clutch is engaged, the right-hand input controller is not able to select an icon or control an instrument. In this configuration, the right-hand input controller can be moved, for example into a more convenient position, without the instrument previously operatively coupled to that input device also moving. The icons associated with the right-hand input device 1302, 1304, 1306 are greyed out, or are partly transparent, as a result of the right-hand input device clutch being engaged.

When the right-hand input device clutch is engaged, the left-hand input device can remain operatively coupled to the respective instrument. This is indicated in FIG. 13 by the active icon 1308 (in respect of the instrument operatively coupled to the left-hand input device) being displayed in a solid colour. Suitably the same is true when the left-hand input device clutch is engaged, i.e. the right-hand input device remains operatively connected to an instrument. In other examples, a clutch can engage for both the left-hand input device and the right-hand input device at the same time. This may be because a separate clutch for each of the input devices is engaged, or caused to be engaged, simultaneously, or because a single clutch can be engaged in respect of both input devices.

Suitably the control system is configured to determine whether a user is holding an input device. For example, the input device 304 suitably comprises a sensor 440 for determining whether a user is holding the input device. The sensor can be any suitable sensor such as a touch sensor, for example a capacitive sensor, a temperature sensor, a light sensor, an infrared sensor, a switch, and so on. Any combination of these types of sensors can be used.

Suitably, the control system is configured to cause the graphical arrangement of icons to provide an indication where an input device is not being held. For example, as illustrated in FIG. 14, the graphical arrangement of icons can comprise warning icons 1402, 1404 indicating that the input devices are not being held. A left-hand warning icon 1402, indicating that the left-hand input device is not being held, may comprise an indication of the left hand (or it may indicate that it is related to the left hand and/or the left-hand input device in some other way, additional or alternative to being displayed on the left-hand side of the display). A right-hand warning icon 1404, indicating that the right-hand input device is not being held, may comprise an indication of the right hand (or it may indicate that it is related to the right hand and/or the right-hand input device in some other way, additional or alternative to being displayed on the right-hand side of the display).

The control system is suitably configured to determine that a warning condition has been entered. The control system is suitably configured, in response to this determination, to cause the display of a warning icon (or an icon otherwise representative of the warning condition) in the region of the graphical arrangement of icons that is associated with the system, for example the system region as discussed above. The warning icon can comprise a warning triangle 1406. This is illustrated in FIG. 14. This can alert the user to the presence or existence of the warning condition. Criteria relating to the warning condition can be selected as desired. Suitably the warning condition is indicative of console faults or system-level faults. The control system is suitably configured to monitor such criteria, and in dependence thereon, to cause the display of the warning icon.

More generally, where there is a system-wide condition or alert, for example a warning condition, the control system can cause the display of an icon, for example a warning icon, in the system region. Since icons displayed in this region relate to the system in general, they are suitably larger than the menu icon and the imaging device icon. Suitably icons displayed in the system region comprise a single icon.

The control system 308 suitably comprises a kinematics controller 310 configured to determine an interface state in dependence on the one or more state signal associated with the plurality of instruments. The interface state comprises data associated with the graphical arrangement of icons for display.

Suitably the kinematics controller 310 is configured to process telemetry data to render the icon. In other words, the telemetry data is processed as normal by the control system 308. This ensures that processing associated with rendering the graphical arrangement of icons does not affect data relied on by any other portion of the system. Suitably, the output of processing carried out for the purposes of rendering the graphical arrangement of icons is used just to render the graphical arrangement of icons. Suitably nothing else depends on the icon data. Thus data that is critical to the operation of the robotic system is not affected by the icon processing or rendering. The icon rendering or processing can be carried out downstream of the standard data processing. This permits maintaining safety of operation.

Suitably, the control system 308 comprises a visual processor 312 configured to receive the interface state from the kinematics controller 310 and to render the graphical arrangement of icons for display. The kinematics controller 310 is suitably operable at a higher frequency than the visual processor 312. In a preferred example, the interface for display on the display device 306 is generated by the visual processor 312. The visual processor is suitably separate from the kinematics controller 310. The visual processor may be concerned only with image output. I.e. no critical system in the robotic system depends on the output of the visual processor.

The control system may be operable in a continuous fashion. The visual processor is suitably operable in a continuous fashion. The visual processor is suitably configured to generate the interface for display in a continuous fashion. Thus the kinematics controller can be configured to continuously output data, and the interface can be continuously generated in dependence on the data output by the kinematics controller. In some examples, the visual processor need not operate continuously. It may be sufficient for the visual processor to operate at the frame rate at which the interface generated by the visual processor is to be displayed.

The visual processor 312 need not operate at the same frequency as the control system 308 and/or the kinematics controller 310. The visual processor can be configured to operate at a lower frequency than the control system and/or the kinematics controller. The frequency at which the visual processor is configured to operate suitably depends on the desired frame refresh rate of the displayed image. Suitably the frequency at which the visual processor is configured to operate is equal to or greater than the desired frame refresh rate.

The control system and/or kinematics controller may be required to operate at a relatively higher frequency (which might be in the order of several hundreds of Hertz) so as to satisfy safety requirements. The frame refresh rate of the displayed image is likely to be much lower than this, and in one example is of the order of 120 Hertz, or 60 Hertz. Operating the visual processor at a slower operating frequency can be more efficient in terms of processing. This can mean that a slower processor can be used as the visual processor. Suitably the frequency of operation of the visual processor 312 and/or the frame refresh rate of the displayed image is higher than a human perception limit, so that the icon rendering and changes appear smooth.

As mentioned above, the kinematics controller is configured to perform the analysis and calculations on the input data and to output data on which the icon rendering can be based. That is to say, the kinematics controller outputs data corresponding to what should be displayed on the display device as part of the displayed image. The kinematics controller is suitably configured to output data indicating the state of one or more instruments, data indicating the selectability of one or more instruments, data indicating a control mode of one or more instruments and/or data relating to the graphical arrangement of icons. The kinematics controller thus handles the interface state. The interface state comprises information necessary to render the display, including the graphical arrangement of icons. The visual processor is configured to perform the necessary processing of the information output by the kinematics controller so as to generate the displayed image, including the graphical arrangement of icons. The visual processor performs the processing and rendering to generate the interface according to the interface state output by the kinematics controller. This can relieve the burden on the kinematics controller by shifting the image processing to the visual processor. The output from the kinematics controller need not be calculated specifically for the purpose of generating the graphical arrangement of icons and/or interface. Suitably the visual processor is configured to generate the interface in dependence on data output by the kinematics controller in the course of its normal operations (i.e. without carrying out additional operations relating to and/or exclusively for the purpose of rendering the interface).

As described above, the icons in the graphical arrangement of icons may be coloured to match a colour of at least one of the end effector, the instrument and the robot arm to which that instrument is coupled. The visual processor is suitably configured to generate the icons in the graphical arrangement of icons so as to match at least one of the end-effector, the instrument and the robot arm. For example, the visual processor is configured to match a visual indication such as a pattern, orientation, profile and/or colour. In some examples, colours can be applied to the instruments, or at least portions of the instruments that will appear in the image captured by the imaging device, such as the end effector and/or the distal portion of the instrument shaft. The icons can be rendered to match these colours. Thus, a particular instrument shaft can be coloured green, and the icon on the display corresponding to that instrument can also be coloured green. This permits a quick and intuitive identification of the correspondence between the instrument and the icon. The colour can be chosen in dependence on the instrument type, for example all gripper instruments can be coloured green. Alternatively a series of colours can be chosen for each type of instrument. The colours chosen for one type of instrument are suitably different from the colours chosen for another type of instrument, though this need not be the case. For example, where an electrosurgical instrument is to be used together with two gripper instruments, the electrosurgical instrument may be coloured white, one gripper instrument may be coloured green and the other gripper instrument may be coloured blue. A desired colouring can be applied to the instruments by any suitable colour-application process, such as physical vapour deposition to colour stainless steel and anodising to colour aluminium.

The colour to apply to the icon in the display can be determined on the basis of data stored in a radio frequency identification (RFID) tag on the instrument. The control system is suitably configured to query the data stored in the RFID tag. The stored data suitably comprises the colour corresponding to that instrument. Thus, the control system can match the colour of the icon to that of the instrument in dependence on the stored data.

The instrument itself need not be coloured. The colour can be applied virtually, for example on the displayed image. Thus, the control system is suitably configured to determine a colour to associate with the instrument, on the basis of data stored in an RFID tag on the instrument, or in any other suitable way, and to generate an overlay on or as part of the displayed image to colour the instrument. The whole of the instrument visible in the displayed image need not be virtually coloured. Suitably, to avoid obscuring the operation of the end effector, the end effector is not virtually coloured. Suitably the control system is configured to apply colour to a more limited region associated with the instrument, for example an area such as a circular area on the instrument shaft, away from the end effector. More generally, the virtual colour can be applied to a flag associated with the instrument, which need not exactly align with the outline of the instrument viewed on the display. The generation of the overlay, or the application of the virtual colouring, is suitably handed by the visual processor.

In one example, the colour of at least a portion of the robot arm or instrument is dynamically variable. For example, the robot arm or instrument may comprise a colour band. The colour band may comprise a portion of a coloured material, such as plastic or metal. The colour band may be removably mounted to the instrument or the robot arm. The colour band may comprise a display portion configured to show a colour. The display portion is suitably a screen, an LED, or an array such as an LED array. The LED may be a multicolour LED. The LED array may comprise a plurality of single-colour LEDs, a plurality of multicolour LEDs, or one or more single-colour LED and one or more multicolour LED. The display portion is suitably responsive to a colour control signal, for example based on data stored in an RFID tag, to control the colour shown by the display portion.

Figure 9:
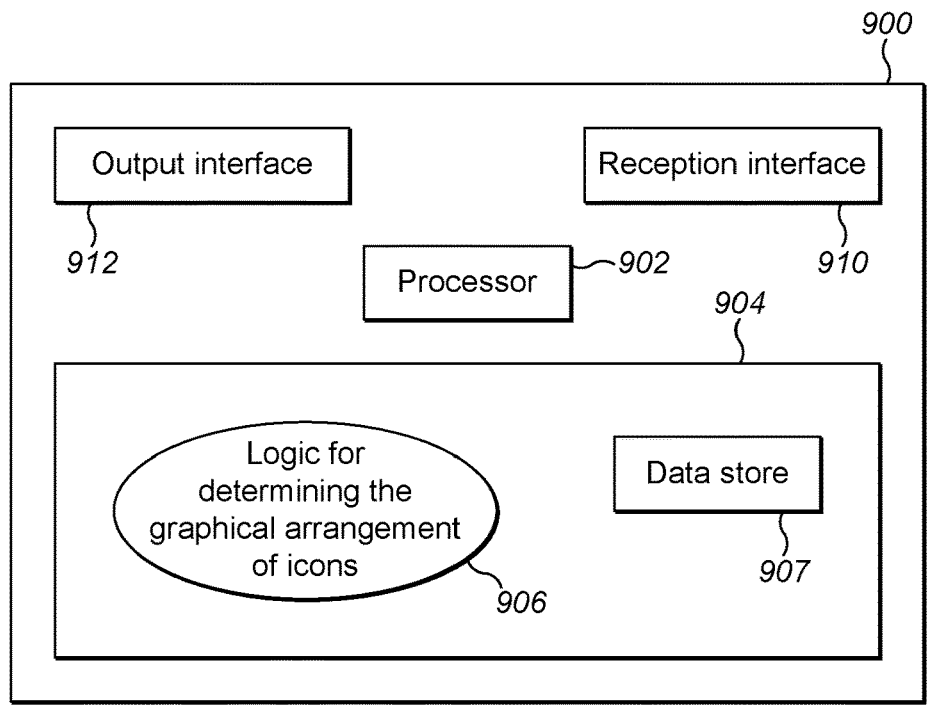
FIG. 9 schematically illustrates a computing-based device.

Reference is now made to FIG. 9. FIG. 9 illustrates a computing-based device 900 in which the robotic surgical system 300 can be implemented. The computing-based device may be an electronic device. The computing-based device illustrates functionality for receiving one or more state signal, a mode change signal and a select signal. The computing-based device illustrates functionality for storing the received signals, determining a graphical arrangement of icons for display, and outputting a display signal to cause the graphical arrangement of icons to be displayed. The computer-based device suitably includes functionality to enable control of a selected instrument by the surgeon console.

Computing-based device 900 comprises a processor 902 for processing computer executable instructions configured to control the operation of the device in order to perform the methods described herein. The computer executable instructions can be provided using any computer-readable media such as memory 904. Further software that can be provided at the computer-based device 900 includes logic 906 for determining the graphical arrangement of icons. Alternatively, the logic 906 is implemented partially or wholly in hardware. A data store 907 may store data such as one or more state signal, mode change signals and/or select signals.

Computing-based device 900 further comprises a reception interface 910 for receiving the one or more state signal, the mode change signal and/or the select signal. Computing-based device 900 further comprises an output interface 912 for outputting the determined graphical arrangement of icons to the display device for display, and/or outputting a control signal to effect control of the selected instrument by the surgeon console. FIG. 9 illustrates a single computing-based device in which the robotic surgical system 300 is implemented. However, the functionality of the robotic surgical system 300 may be implemented on separate computing-based devices.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A control system configured to control a surgical robot by a surgeon console remote from the surgical robot, the control system being configured to:
   receive one or more state signal associated with a plurality of instruments, each of the plurality of instruments being attachable to the surgical robot, the one or more state signal indicating:
      a selectability of each of the plurality of instruments for control by the surgeon console, and
      a control mode of each of the plurality of instruments from a group of modes, the group of modes comprising:
         a manipulation mode in which an instrument of the plurality of instruments is controllable by the surgeon console, and
         a selection mode in which an instrument of the plurality of instruments is selectable for control by the surgeon console;
   determine a graphical arrangement of icons for display in dependence on the received one or more state signal, where each icon represents a respective one of the plurality of instruments, and output a display signal to cause the graphical arrangement of icons to be displayed;
   receive a mode change signal indicating a change of mode to the selection mode;
   modify, in response to the received mode change signal, the graphical arrangement of icons to permit identification of selectable instruments of the plurality of instruments;
   receive a select signal from the surgeon console indicating a selection of one of the selectable instruments;
   modify, in response to the received select signal, the graphical arrangement of icons to permit identification of the selected instrument; and
   enable control of the selected instrument by the surgeon console.

2. A control system according to claim 1, in which the graphical arrangement of icons comprises:
   a list region in which an icon representing one of the plurality of instruments is caused to be displayed prior to the change of mode to the selection mode, and
   a selection region in which an icon representing a selectable instrument of the plurality of instruments is caused to be displayed in the selection mode;
the list region and the selection region being at least partially non-overlapping.

3. A control system according to claim 2, in which the graphical arrangement of icons comprises an image region for displaying an image of a surgical site, the image region being provided towards a centre of the graphical arrangement of icons, and in which the selection region is provided so as to at least partially overlap the image region.

4. A control system according to claim 3, in which the list region is at least partially non-overlapping with the image region.

5. A control system according to claim 3, in which the list region comprises a new instrument region in which an icon representing a newly-added instrument is caused to be displayed, the new instrument region being provided so as to at least partially overlap the image region.

6. A control system according to claim 3, configured to receive an image signal representative of an image from a surgical site, and to cause the display of the image in the image region, the displayed image comprising an instrument image of an instrument at the surgical site, and the control system being configured to modify the instrument image in response to receiving the mode change signal.

7. A control system according to claim 6, configured to modify the instrument image by at least one of overlaying graphics on the image region, modifying graphics overlaid on the image region, and removing graphics overlaid on the image region.

8. A control system according to claim 6, configured to modify the instrument image to correspond to the modification to the graphical arrangement of icons permitting identification of the selectable instruments.

9. A control system according to claim 2, in which the list region is provided one of at and towards a periphery of the graphical arrangement of icons.

10. A control system according to claim 2, configured, in response to receiving the mode change signal, to cause a transition of the icon representing the selectable instrument to the selection region to indicate that the respective instrument is selectable, wherein optionally the control system is configured to cause the transition to be a continuous transition.

11. A control system according to claim 2, configured to receive an input signal from each of a plurality of input devices of the surgeon console, the graphical arrangement of icons comprising a plurality of selection regions with each input device being associated with a respective one of the plurality of selection regions, the control system being configured, in response to receiving the mode change signal, to cause icons representing instruments selectable by each input device to be displayed in the respective selection region for that input device.

12. A control system according to claim 2, in which at least one of the list region, the selection region and the new instrument region comprises a border around at least a portion of its periphery, and the control system is configured to modify the border in response to receiving the mode change signal to permit identification of the change of mode.

13. A control system according to claim 1, configured to receive the mode change signal from at least one of the surgeon console and the surgical robot.

14. A control system according to claim 1, configured, in response to receiving the mode change signal, to change to the selection mode from one of the manipulation mode and a setup mode in which an instrument of the plurality of instruments is set up for operative coupling to the surgeon console.

15. A control system according to claim 1, in which the modification to the graphical arrangement of icons permitting identification of the selectable instruments comprises one or more of:
   changing the colour of an icon,
   changing the size of the icon,
   changing the background of the icon,
   changing the icon from a two-dimensional icon to a three-dimensional icon,
   changing the icon from a three-dimensional icon to a two-dimensional icon,
   causing the icon to flash, and
   causing the icon to flash with a modified frequency.

16. A control system according to claim 1, comprising a kinematics controller configured to determine an interface state in dependence on the one or more state signal associated with the plurality of instruments, the interface state comprising data associated with the graphical arrangement of icons for display.

17. A control system according to claim 16, comprising a visual processor configured to receive the interface state from the kinematics controller and to render the graphical arrangement of icons for display, the kinematics controller being operable at a higher frequency than the visual processor.

18. A control system according to claim 1, in which an icon of the graphical arrangement of icons comprises a cluster of icons.

19. A method for controlling a surgical robot by a surgeon console remote from the surgical robot, the method comprising:
   receiving one or more state signal associated with a plurality of instruments, each of the plurality of instruments being attachable to the surgical robot, the one or more state signal indicating:
      the selectability of each of the plurality of instruments for control by the surgeon console, and
      a control mode of each of the plurality of instruments from a group of modes, the group of modes comprising:
         a manipulation mode in which an instrument of the plurality of instruments is controllable by the surgeon console, and
         a selection mode in which an instrument of the plurality of instruments is selectable for control by the surgeon console;
   determining a graphical arrangement of icons for display in dependence on the received one or more state signal, where each icon represents a respective one of the plurality of instruments, and outputting a display signal to cause the graphical arrangement of icons to be displayed;
   receiving a mode change signal indicating a change of mode to the selection mode;
   modifying, in response to the received mode change signal, the graphical arrangement of icons to permit identification of selectable instruments of the plurality of instruments;
   receiving a select signal from the surgeon console indicating a selection of one of the selectable instruments;
   modifying, in response to the received select signal, the graphical arrangement of icons to permit identification of the selected instrument; and
   enabling control of the selected instrument by the surgeon console.

20. A non-transitory computer readable storage medium having stored thereon machine readable code that, when executed at a computer system, causes the computer system to implement a method for controlling a surgical robot by a surgeon console remote from the surgical robot, the method comprising:
   receiving one or more state signal associated with a plurality of instruments, each of the plurality of instruments being attachable to the surgical robot, the one or more state signal indicating:
      the selectability of each of the plurality of instruments for control by the surgeon console, and
      a control mode of each of the plurality of instruments from a group of modes, the group of modes comprising:
         a manipulation mode in which an instrument of the plurality of instruments is controllable by the surgeon console, and
         a selection mode in which an instrument of the plurality of instruments is selectable for control by the surgeon console;
   determining a graphical arrangement of icons for display in dependence on the received one or more state signal, where each icon represents a respective one of the plurality of instruments, and outputting a display signal to cause the graphical arrangement of icons to be displayed;
   receiving a mode change signal indicating a change of mode to the selection mode;
   modifying, in response to the received mode change signal, the graphical arrangement of icons to permit identification of selectable instruments of the plurality of instruments;
   receiving a select signal from the surgeon console indicating a selection of one of the selectable instruments;
   modifying, in response to the received select signal, the graphical arrangement of icons to permit identification of the selected instrument; and
   enabling control of the selected instrument by the surgeon console.

* * * * *